(12) United States Patent
Mietzner et al.

(10) Patent No.: US 11,739,289 B2
(45) Date of Patent: Aug. 29, 2023

(54) CONTINUOUS BLADE IMPELLER

(71) Applicant: Lonza Limited, Visp (CH)

(72) Inventors: Michael Mietzner, Fremont, NH (US); Richard Falk, Bend, OR (US); Rajesh Beri, Westford, MA (US); Mark Caswell, Salem, NH (US)

(73) Assignee: Lonza Ltd, Visp (CH)

( * ) Notice: Subject to any disclaimer, the term of this patent is extended or adjusted under 35 U.S.C. 154(b) by 369 days.

(21) Appl. No.: 16/854,183

(22) Filed: Apr. 21, 2020

(65) Prior Publication Data

US 2020/0332241 A1    Oct. 22, 2020

Related U.S. Application Data

(60) Provisional application No. 62/836,922, filed on Apr. 22, 2019.

(51) Int. Cl.
| | | |
|---|---|---|
| *B01F 27/00* | (2022.01) | |
| *C12M 1/06* | (2006.01) | |
| *B01F 27/191* | (2022.01) | |
| *B01F 27/1125* | (2022.01) | |
| *B01F 101/44* | (2022.01) | |

(52) U.S. Cl.
CPC ......... *C12M 27/02* (2013.01); *B01F 27/1125* (2022.01); *B01F 27/191* (2022.01); *B01F 2101/44* (2022.01)

(58) Field of Classification Search
CPC .. C12M 27/02; B01F 27/1125; B01F 2101/44
See application file for complete search history.

(56) References Cited

U.S. PATENT DOCUMENTS

| | | |
|---|---|---|
| 3,476,522 A | 11/1969 | Stovall |
| 4,198,376 A | 4/1980 | Fournel et al. |
| | (Continued) | |

FOREIGN PATENT DOCUMENTS

| | | |
|---|---|---|
| CN | 202081094 | 12/2011 |
| CN | 106281986 | 1/2017 |
| | (Continued) | |

OTHER PUBLICATIONS

Jagani H. et al., "An Overview of Fermenter and the Design Considerations to Enhance Its Productivity", Pharmacologyonline, 2010, pp. 261-301, vol. 1 (41 pages).

(Continued)

*Primary Examiner* — Anshu Bhatia
(74) *Attorney, Agent, or Firm* — Dority & Manning, P.A.

(57) ABSTRACT

An impeller is usable in a variable diameter bioreactor having multiple vessel sections of successively increasing or decreasing volume. The impeller includes an impeller blade extending along an impeller blade axis between first and second axial ends and having opposed impeller blade faces, an impeller blade leading edge, and an impeller blade trailing edge. Each of the leading and trailing edges defines a helix or spiral between the axial ends of the impeller blade. In certain arrangements, the impeller blade is one of at least two impeller blades joined together along an impeller shaft extending axially along the impeller blade axis mentioned, and the helix or spiral has a pitch approximately equal to one half of a length between the first and second axial ends.

15 Claims, 37 Drawing Sheets

(56) References Cited

U.S. PATENT DOCUMENTS

| | | |
|---|---|---|
| 4,307,196 A | 12/1981 | Pozzi |
| 4,906,577 A | 3/1990 | Armstrong et al. |
| 5,002,890 A | 3/1991 | Morrison |
| 8,951,785 B2 | 2/2015 | Fatherazi et al. |
| 9,670,446 B2 | 6/2017 | Khan |
| 9,783,771 B2 | 10/2017 | Khan |
| 2003/0147304 A1 | 8/2003 | Schuchardt et al. |
| 2007/0237024 A1* | 10/2007 | Brod ............... B01F 27/85 366/241 |
| 2009/0050562 A1* | 2/2009 | Novak ............... C02F 3/206 210/627 |
| 2009/0071336 A1* | 3/2009 | Jernberg ............ B01F 27/1142 366/314 |
| 2013/0189767 A1 | 7/2013 | Cheng et al. |
| 2017/0267962 A1 | 9/2017 | Khan |
| 2017/0292102 A1 | 10/2017 | Abraham et al. |
| 2017/0349874 A1 | 12/2017 | Jaques et al. |
| 2017/0369828 A1 | 12/2017 | Mietzner et al. |

FOREIGN PATENT DOCUMENTS

| | | |
|---|---|---|
| WO | WO 2017/207822 A1 | 12/2017 |
| WO | WO 2017/223269 A1 | 12/2017 |

OTHER PUBLICATIONS

Ameur H., et al. "Hydrodynamics in a Vessel Stirred by Simple and Double Helical Ribbon Impellers", Central European Journal of Engineering, 2013, pp. 87-98, vol. 3, No. 1, Versita (12 pages).

International Search Report for PCT/US20/29189 dated Jul. 6, 2020, 9 pages.

ESSR for EP20795835 dated Dec. 7, 2022, 13 pages.

* cited by examiner

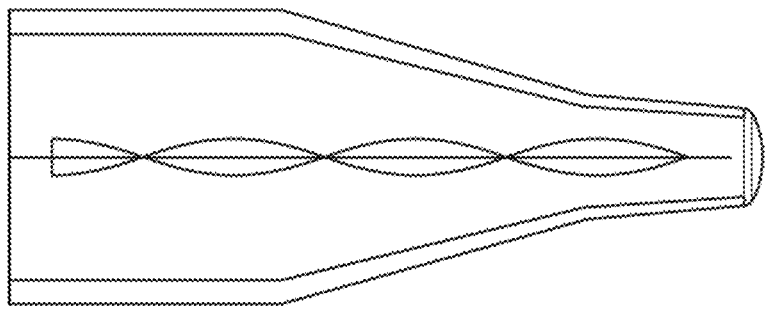
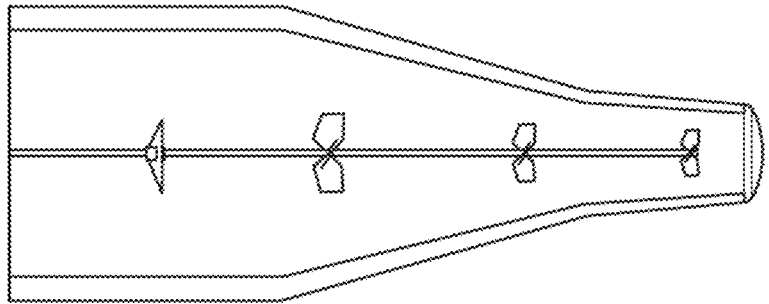
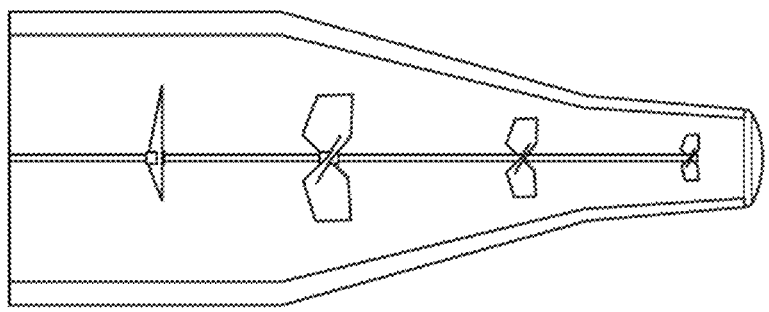
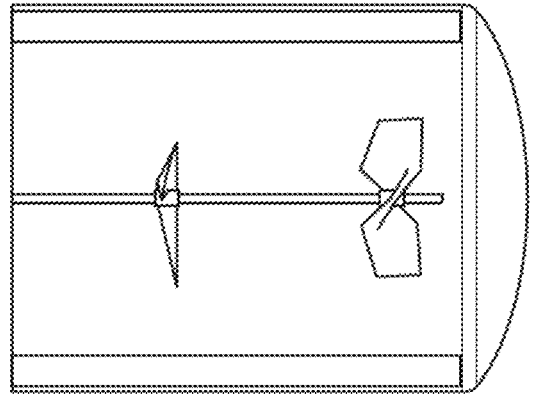
Schematics of 20,000 L (A) conventional bioreactor, (B, C) VDB with conventional impellers, and (D) VDB with continuous agitator.

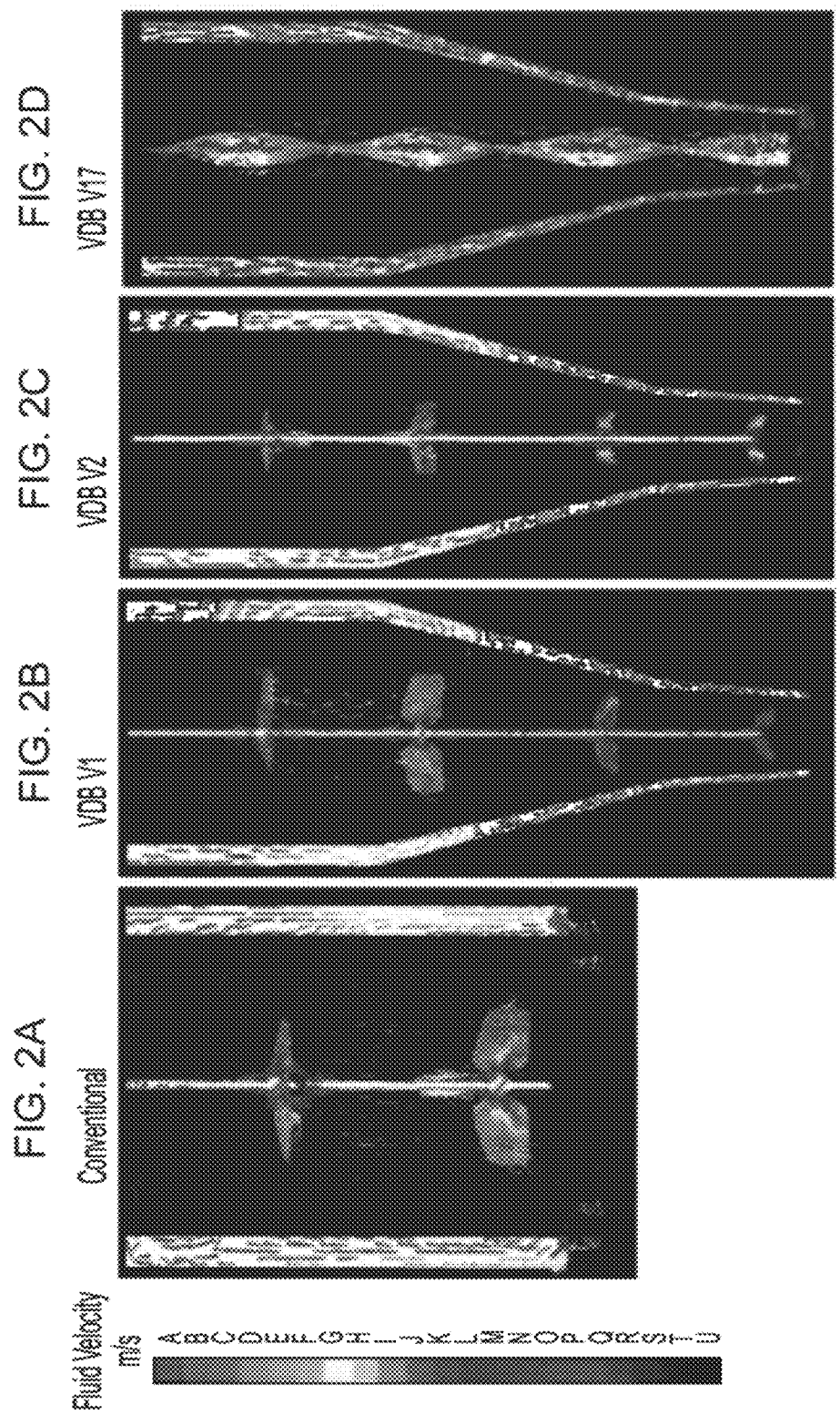

Initial position of tracer for CFD simulations of mixing time.

Calculated blend times from CFD simulations.

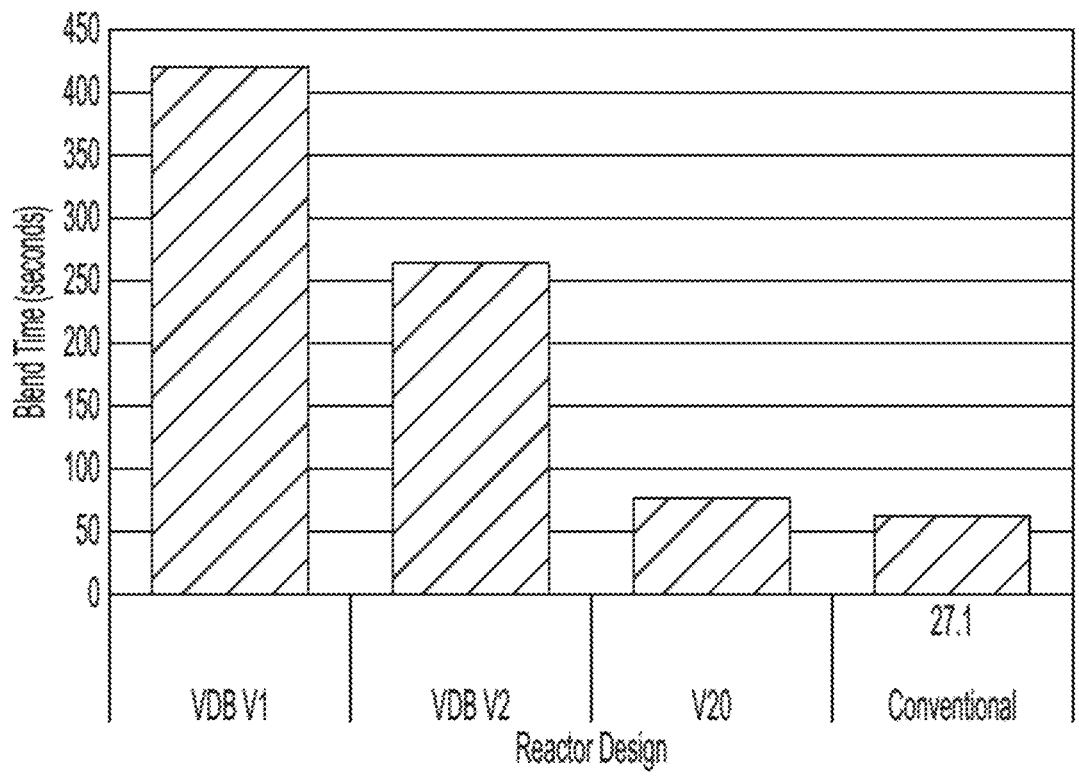

FIG. 4B

VDB Modeling Update

- Summary of Results
  - The addition of a second impeller (a hydrofoil) below the continuous impeller (design V6) resulted in marginal gains in reducing blend time.
  - Increasing the pitch from 1 to 2 revolutions up the shaft length (design V7) reduced blend time to a greater extent than did design V6.
  - Increasing the pitch from 1 to 2 revolutions <u>and</u> adding a second "flight" to the continuous impeller (design V8) resulted in the largest reduction in blend time (82 seconds compared to 62 seconds for the conventional 20kL reactor at similar P/V values).

- Additional design changes to promote axial turnover at bottom of reactor
  - Increase pitch of continuous impeller in the 1kL section of the reactor.
  - Increase depth of continuous impeller into 1kL section (possibly eliminate conventional impeller).

FIG. 5

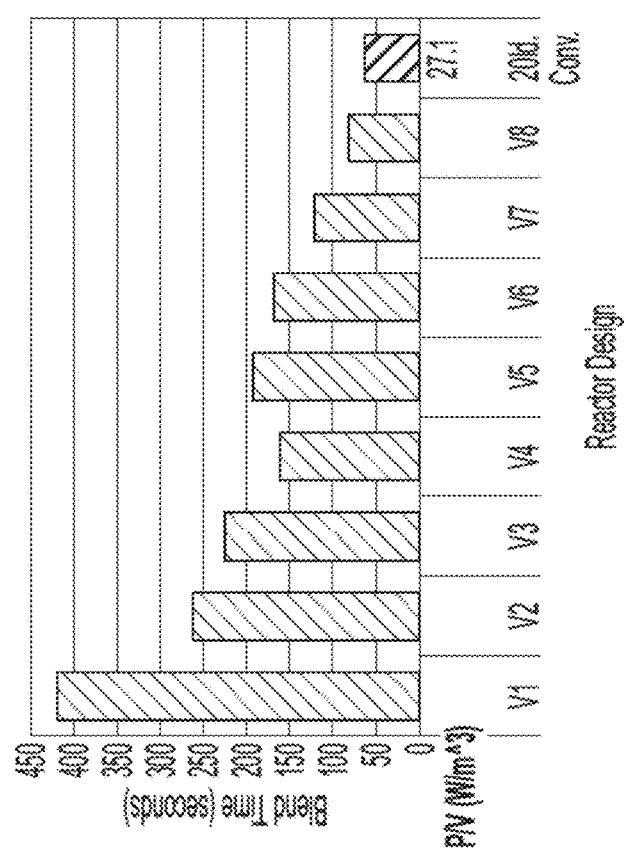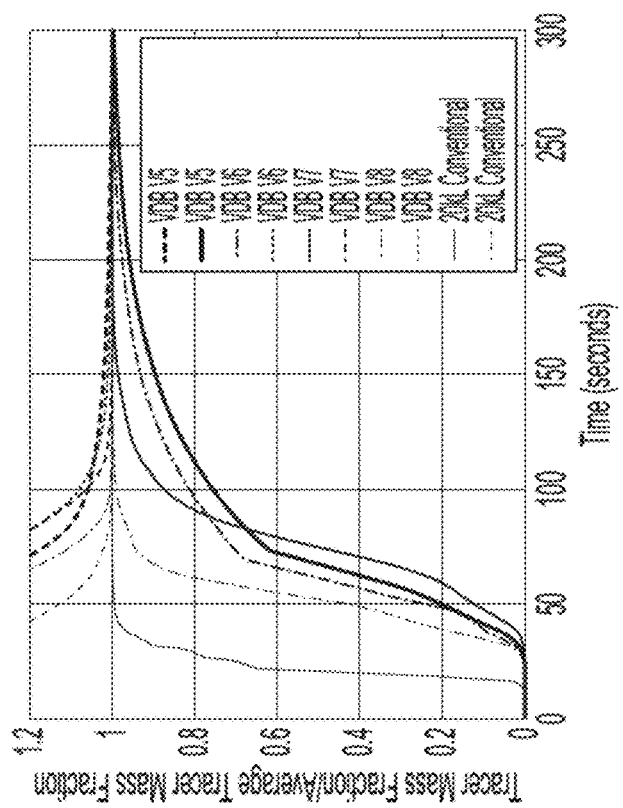
FIG. 8

VDB Modeling Update

- Summary of Model Results
  - Analysis of slightly increased impeller diameter at reactor top (V9, V16-V20)
    - V19 and V20 were created to further increase the diameter of the impeller at the top
    - V20 shows a blend time of 68.7 seconds (subject to verification).
    - V19 was erroneously given only 1 blade instead of 2 and showed a blend time of 102.5 seconds. (subject to re-running)

- Potential Final Modeling Steps
  - Re-run V19 and V20.
  - Once last iteration is complete:
    - Determine impeller speed for target P/V at 1kL and 4kL fills
    - Blend time simulations at target P/V for comparison to conventional bioreactors
    - Interface-resolving models of final design and each fill volume to assess for potential for air entrainment

- VDB Prototype Update:
  - Finalized design attributes
    - Entirely 3D printed (to avoid manual construction of baffles, probe ports, joining of sections, etc.) at ¼ wall thickness

FIG. 13

Spatial Analysis of Blend Time Simulation
VDB V20
Vertical Profiles of Normalized Tracer Mass Fraction (unequal Y-axis scaling)
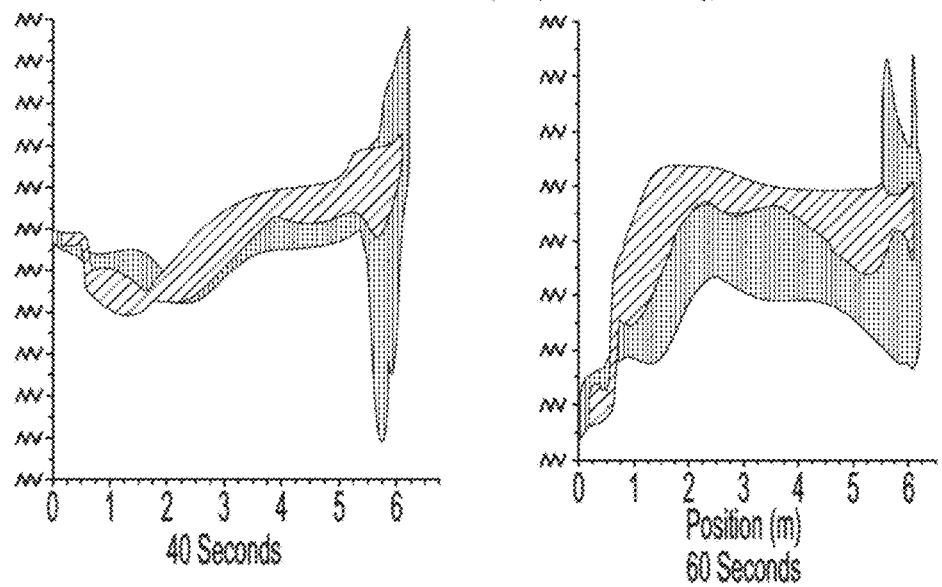
Contour Plots of Normalized Tracer Mass Fraction (unequal scales)
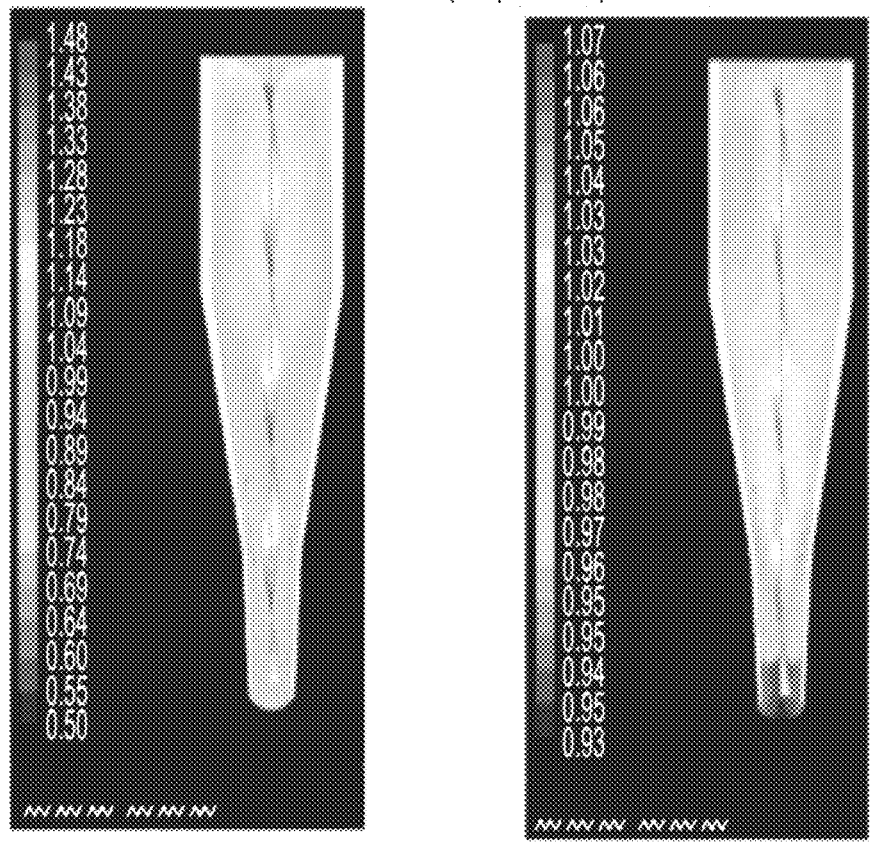
FIG. 17

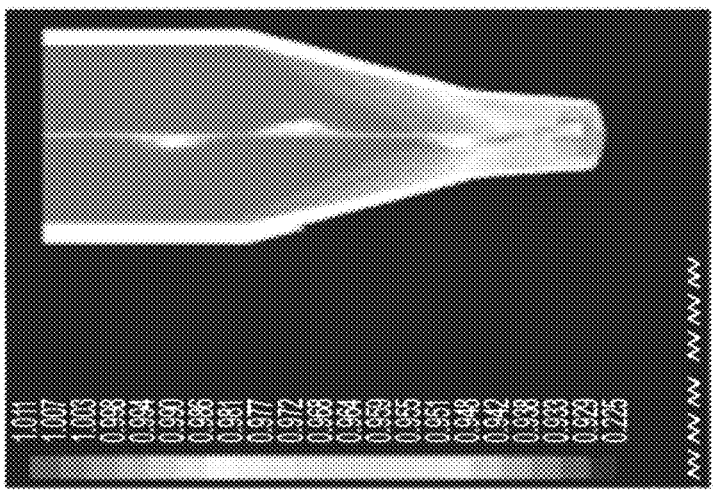
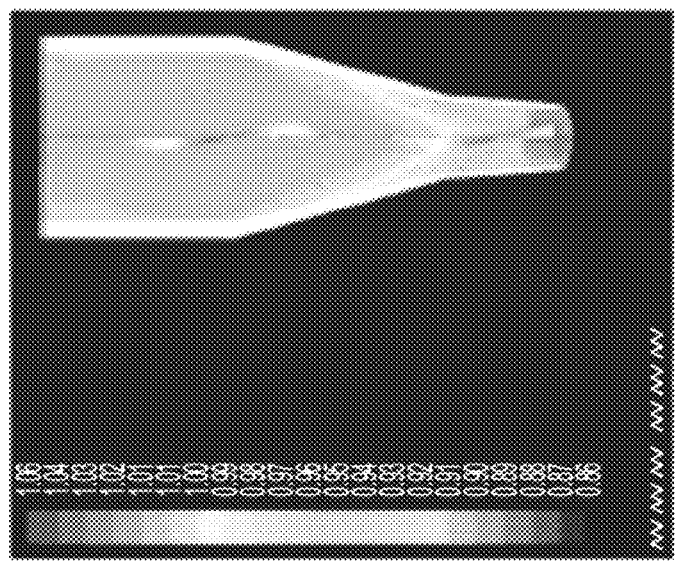
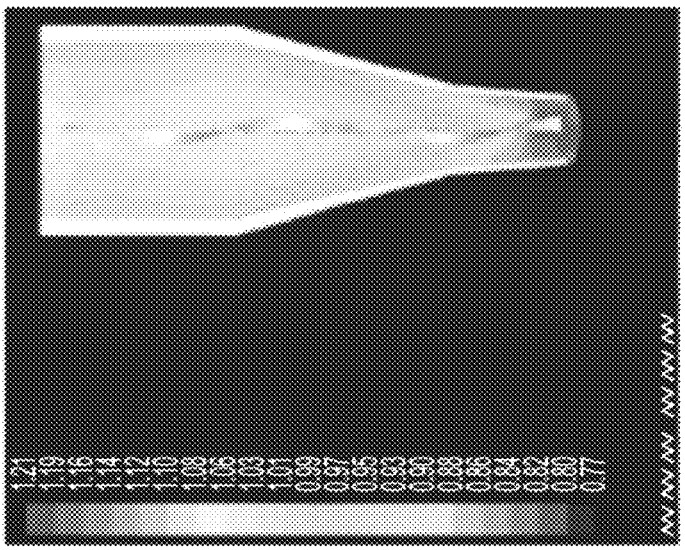
FIG. 18B
Contour Plots of Normalized Tracer Mass Fraction (unequal scales)

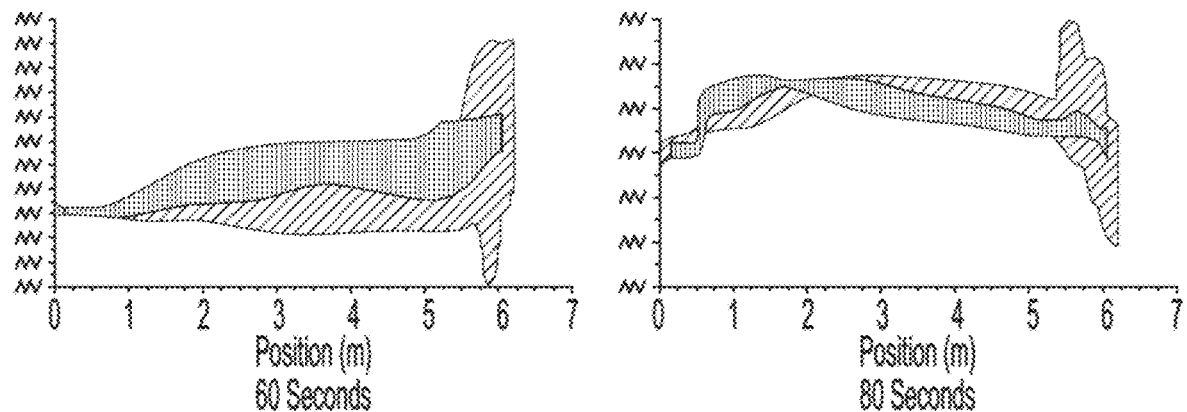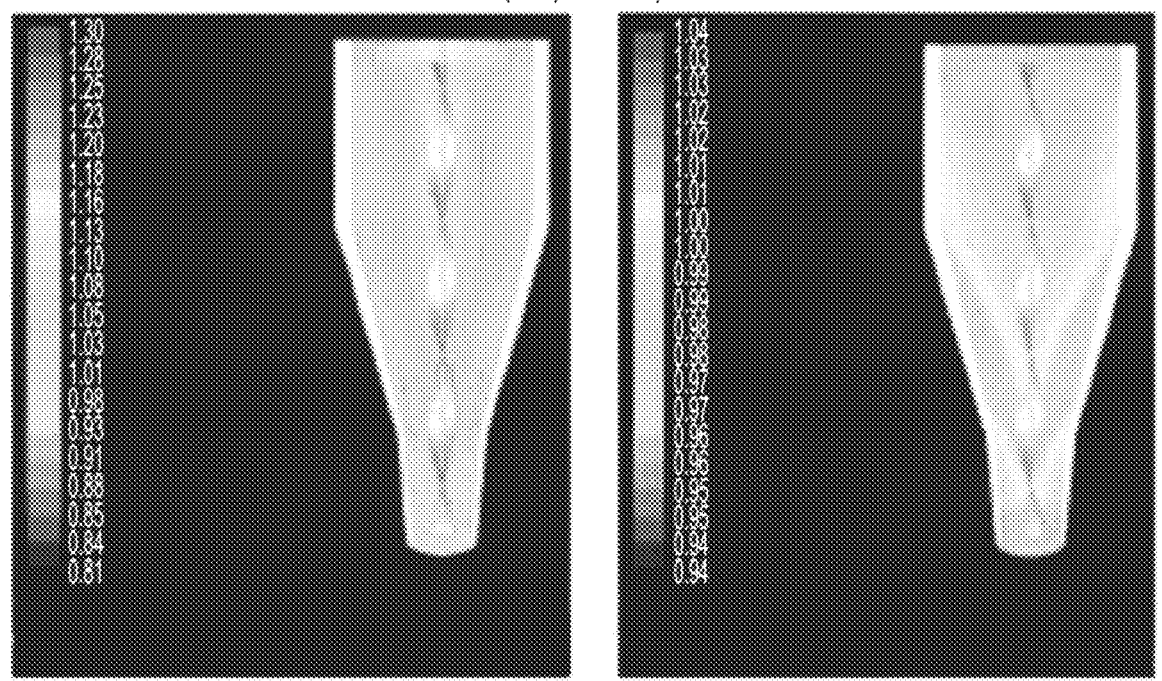
FIG. 19

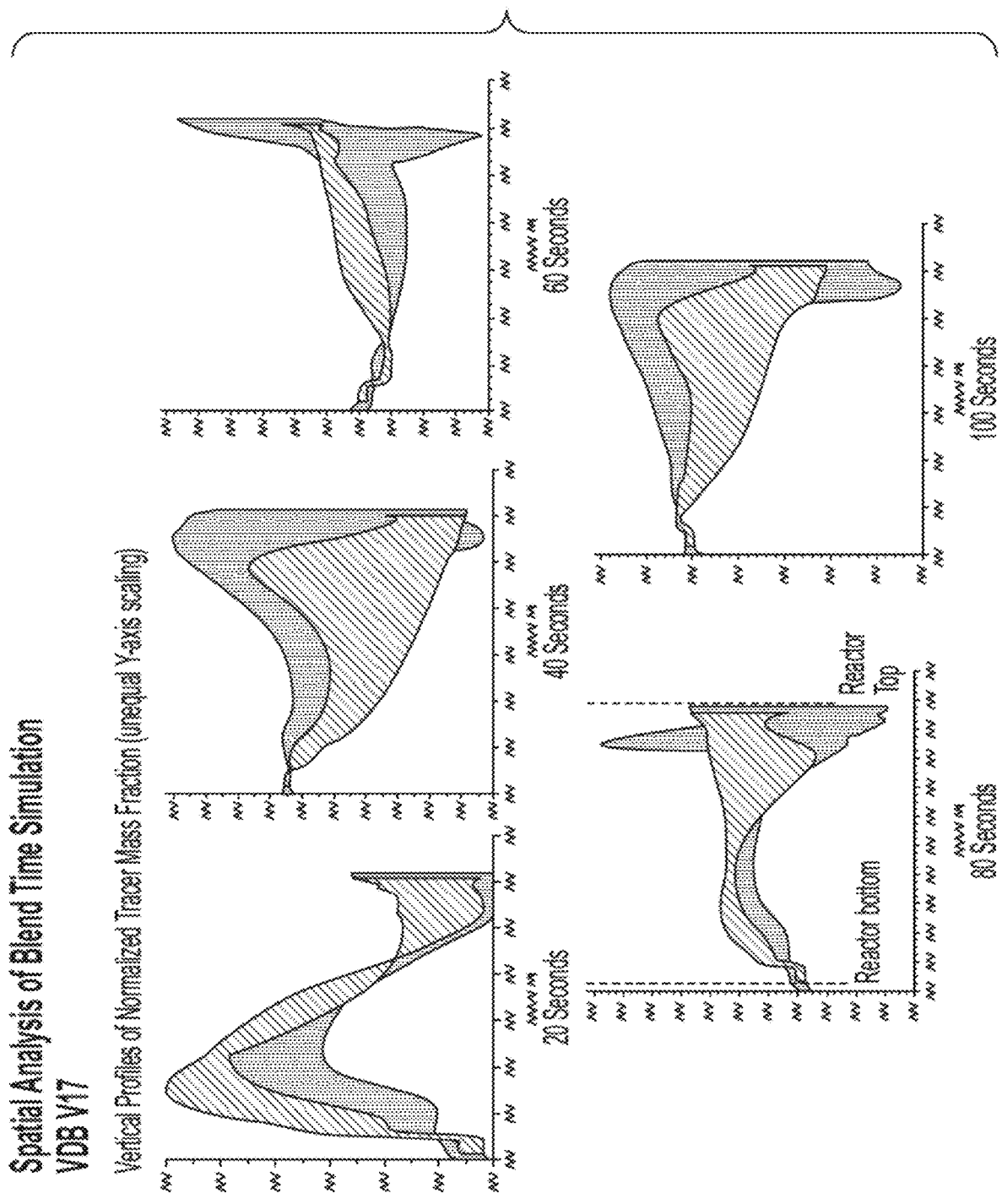

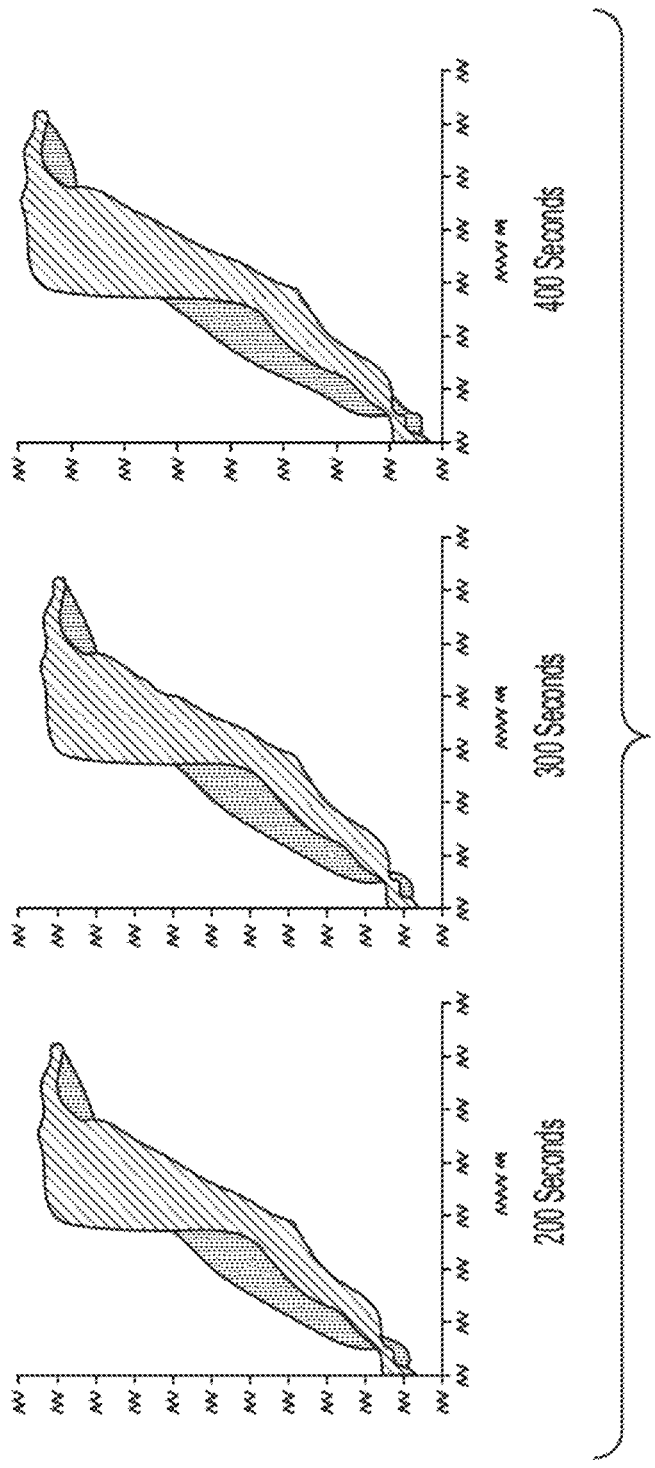

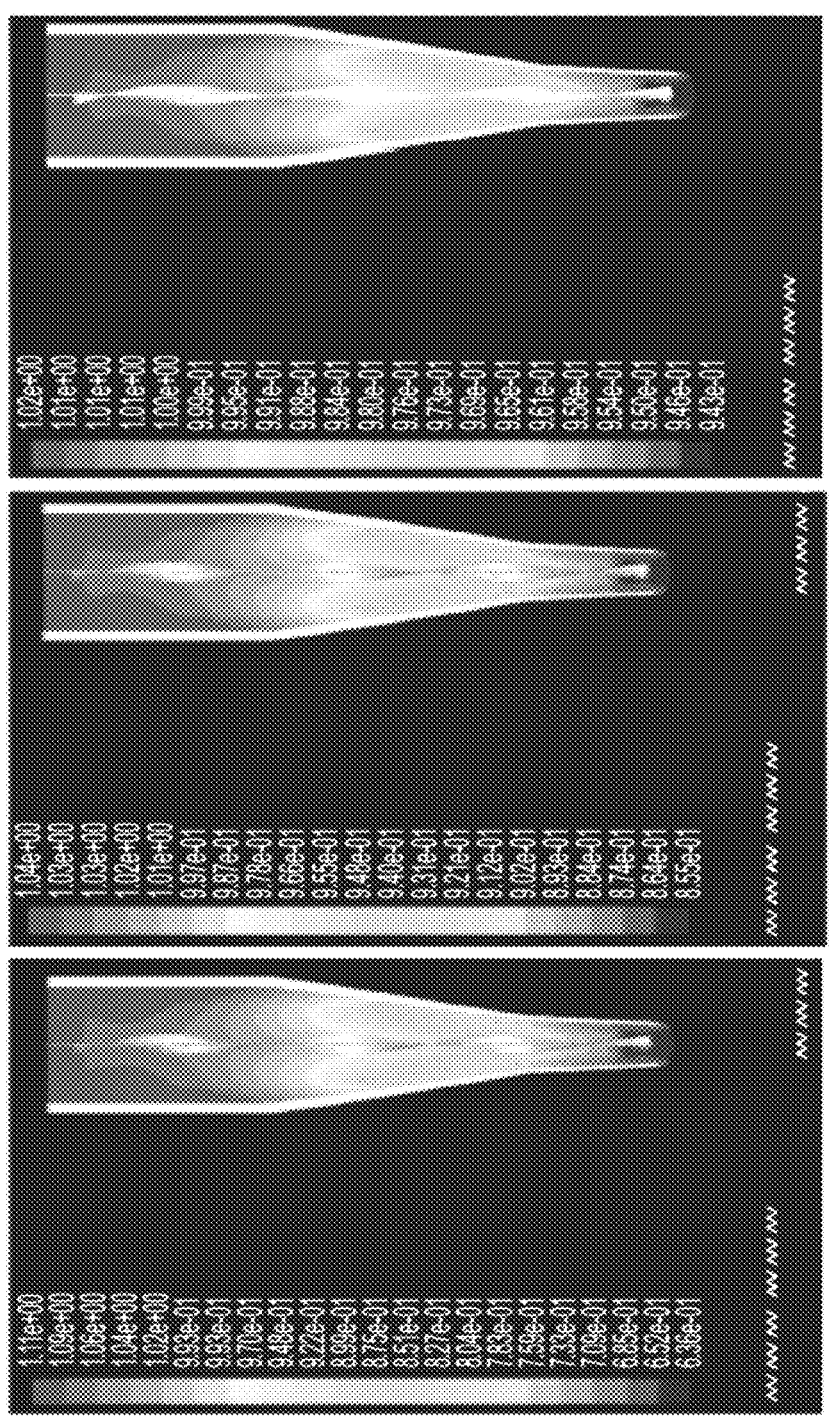
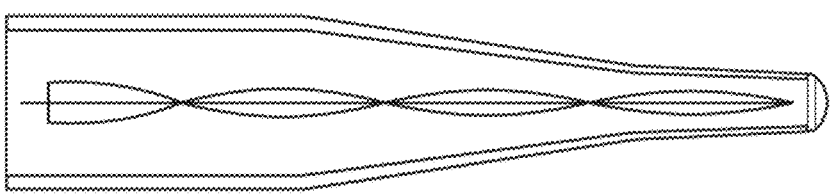
FIG. 21B

VDB Designs V5
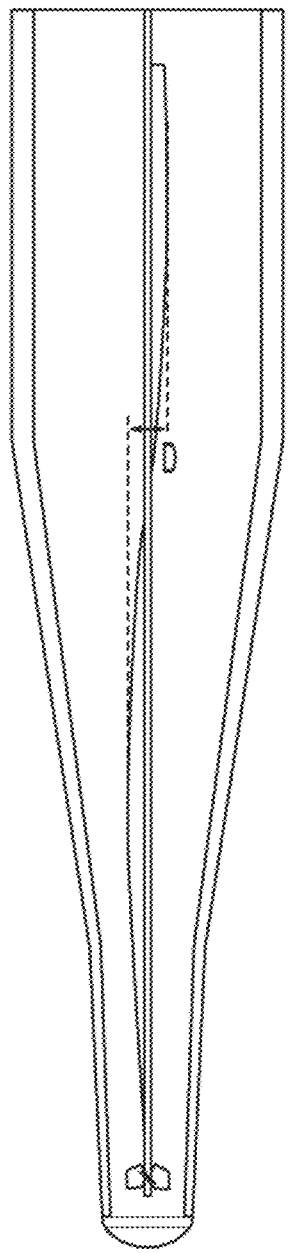
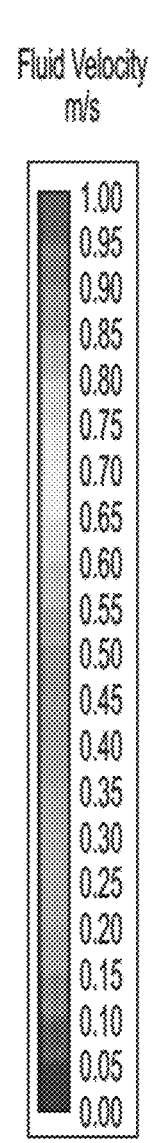
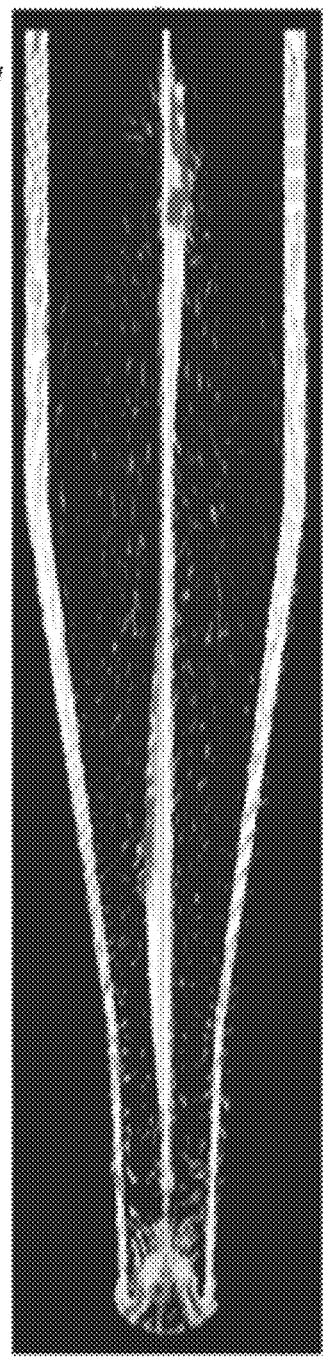
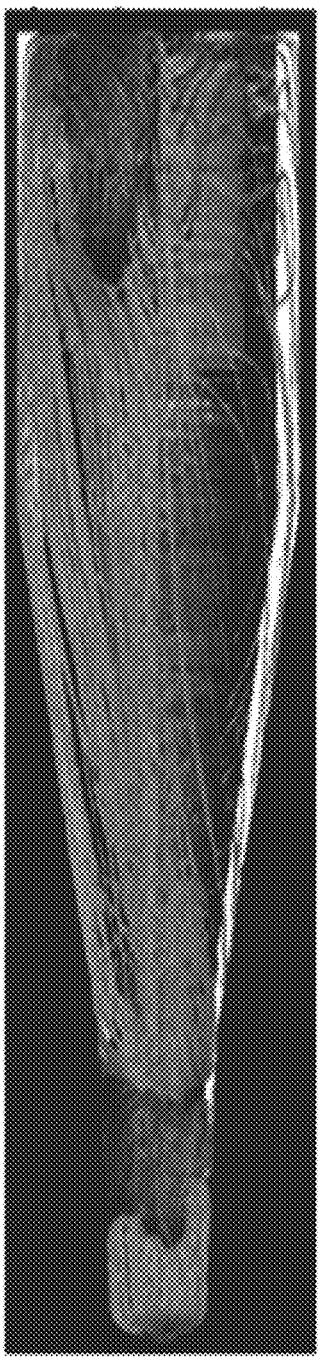
FIG. 28

VDB Designs V6
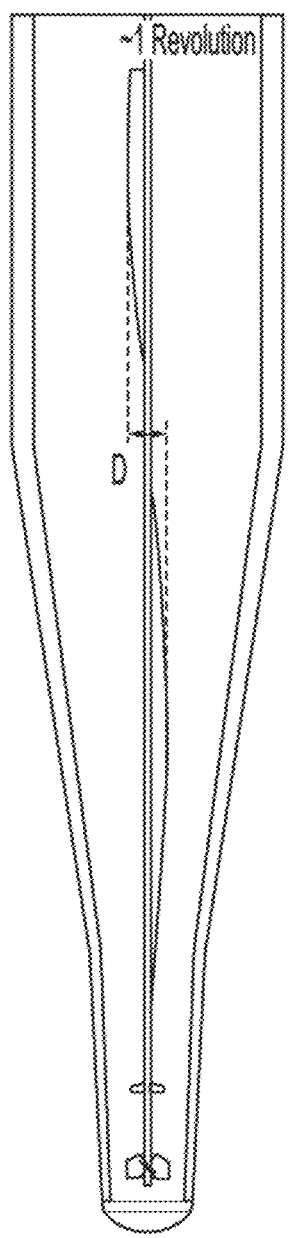
Geometric Representation
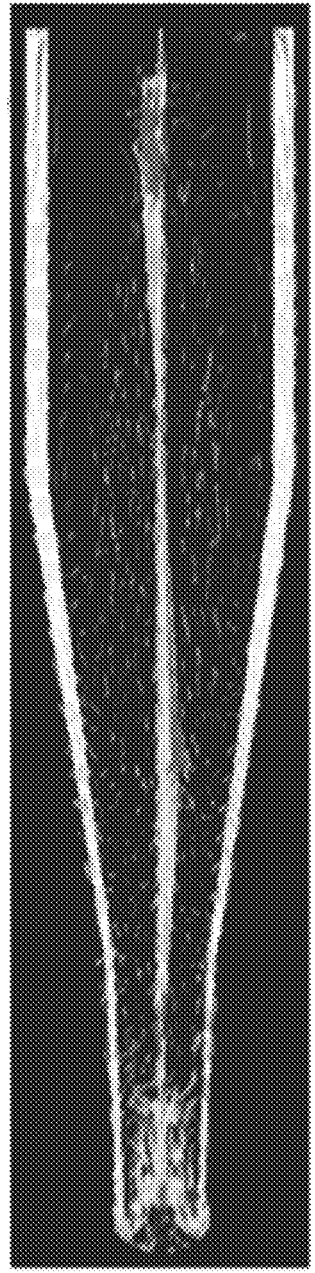
Fluid Velocity Vectors
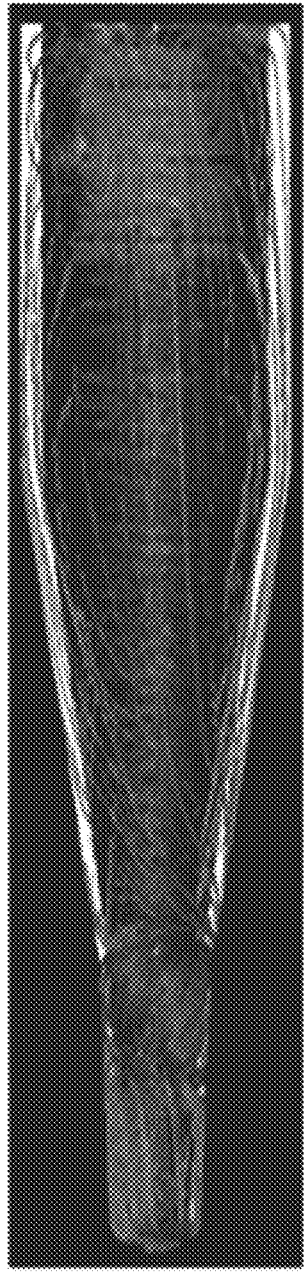
Fluid Pathlines
FIG. 29

CONTINUOUS BLADE IMPELLER

CROSS REFERENCE TO RELATED APPLICATIONS

This application claims priority to and the benefit of U.S. Provisional Application No. 62/836,922, filed Apr. 22, 2019, the contents of which are incorporated herein by reference.

FIELD OF THE INVENTION

The present invention relates to novel impellers for use in bioreactors. Impellers according to the present invention are suitable for use in any type or volume of bioreactor, including variable diameter bioreactors.

DESCRIPTION OF RELATED ART

U.S. Patent Application Publication No. 2017/0369828 A1 to Mietzner et al. discloses certain variable diameter bioreactor vessel configurations for production of biologic material. The bioreactor vessels can include multiple vessel sections with different diameters, and, in certain arrangements, an agitator assembly extends into different bioreactor vessel section internal volumes so that multiple agitators disposed on an agitator shaft are located within respective vessel section internal volumes. The entire disclosure of the Mietzner et al., US 2017/0369828 publication is incorporated herein by reference as non-essential material.

The bioreactors, bioreactor trains, and methods disclosed in U.S. Pat. Nos. 9,783,771; 9,670,446; and U.S. Patent Application Publication No. 2017/0267962 to Khan are also suitable vessels in which the novel impellers of the present invention can be used. These patents and applications are hereby incorporated by reference in their entireties.

The impeller of the present invention may also be used in single-use bioreactors, such as those disclosed in U.S. Patent Application Publication No. 2017/0369828; International Publication No. WO 2017/223269; U.S. Patent Application Publication No. 2017/0349874; and International Publication No. WO 2017/207822.

Traditional bioreactor processing of microorganism cultures typically use multiple impellers installed on a shaft with offset distances between the vessel bottom, the air liquid interface, and between other impellers. Seed vessels (e.g., N-1, N-2) are used to volumetrically bulk up the cell density and volume to production scale. Bioreactor processing at full scale (e.g., N) using traditional impellers, without the use of seed vessels, experience limitations prohibiting consistent volumetric addition of media throughout the growth cycle. A bolus addition is used to achieve a height over the agitator to avoid excessive foaming at the impeller level. Variable diameter bioreactor (VDB) technology also requires a purpose designed impeller to allow consistent volumetric addition and avoid limitations experienced with traditional impellers. This design needs to consider optimal continuous mixing conditions (e.g., mixing time and shear), consistent and appropriate power per unit volume conditions, as well as minimal foaming conditions while providing agitation to a dynamically changing reactor volume to eliminate growth lag from traditional designed agitators. This also allows flexible processing for low, mid, and high titer production lines via varying bioreactor volume to optimize processing at the existing downstream scale.

In some instances, production scale bioreactor processing is accomplished through the use of bioreactors where liquid height is greater than vessel diameter (aspect ratio>1:1, liquid height to vessel diameter) and an array of multiple blade impellers on a shaft are used to mix the culture. Others use aspect ratios disclosed in U.S. Pat. Nos. 9,783,771; 9,670,446; and U.S. Patent Application Publication No. 2017/0267962 to Khan. These bioreactors are designed and sized to scale up the volume of the culture from inoculum in interim seed reactors increasing in volume until production volume has been reached. Typically bioreactors consist of vertical vessels with dished heads and bottoms, either tanks or disposable bags in support structures as necessary. Typically impellers consist of motors coupled with shafts (e.g., mechanical, magnetic) with discrete agitators attached (e.g., welded, set screws) in configurations to mix solutions and gases with culture to promote efficient growth.

There are certain limitations or drawbacks of the known process, product, and apparatus. Each traditional reactor/impeller system involves a transfer from one reactor to another and introduces the culture to conditions that differ from the end of the previous reactor. The reactor/agitator system design works optimally at a narrow volumetric band. This typically produces a "lag phase" effect where the cell growth stalls for a period before attaining exponential growth again. For large scale, this typical processing requires multiple reactors, increased footprint, and increased preparation activities. This leads to increased draw on utilities (water, steam, waste), more clean-in-place (CIP) systems, more steam-in-place (SIP) steps, and greater risk of contamination. There is a limited flexibility in traditional reactor/impeller systems with volumetric scalability. The traditional agitator design applied to the Variable Diameter Bioreactor has been shown to create detached mixing zones (See FIGS. 2A-2C).

SUMMARY OF THE INVENTION

An impeller according to the present invention is particularly suitable for use in a variable diameter bioreactor having multiple vessel sections of successively increasing or decreasing volume. The impeller includes an impeller blade extending along an impeller blade axis between first and second axial ends and having opposed impeller blade faces, an impeller blade leading edge, and an impeller blade trailing edge. Each of the leading and trailing edges defines a helix or spiral between the axial ends of the impeller blade. In certain arrangements, the impeller blade is one of at least two impeller blades joined together along an impeller shaft extending axially along the impeller blade axis mentioned, and the helix or spiral has a pitch approximately equal to one half of a length between the first and second axial ends.

BRIEF DESCRIPTION OF THE DRAWINGS

FIGS. 1A-1D are schematic cross sectional illustrations of 20,000 liter bioreactor vessels, with FIG. 1A showing a conventional bioreactor, FIGS. 1B and 1C showing variable diameter bioreactors (VDBs) with conventional impellers, and FIG. 1D showing a VDB with a continuous agitator or impeller.

FIGS. 2A-2D are schematic representations of fluid velocity vectors at similar values of P/V for 20,000 liter bioreactor vessels, with FIG. 2A showing vectors for a conventional bioreactor, FIGS. 2B and 2C showing vectors for variable diameter bioreactors (VDBs) with conventional impellers, and FIG. 2D showing vectors for a VDB with a continuous agitator or impeller.

FIG. 4B supplies a comparison that is roughly the same as that supplied by FIG. 4, but which includes an updated optimal design.

FIG. 5 is a VDB modelling update, although, again, the analysis had a geometrical issue that was fixed and adjusted in subsequent updates.

FIG. 8 provides a preliminary graphical comparison of blend times of VDB designs relative to a conventional 20,000 kl bioreactor.

FIG. 13 is another preliminary VDB modelling update similar to but more recent than that of FIG. 5.

FIG. 17 illustrates a spatial analysis simulation of blend time for a VDB bioreactor design designated V20.

FIGS. 18A-18B illustrate a spatial analysis simulation of blend time for a VDB bioreactor design designated V19.

FIG. 19 illustrates a spatial analysis simulation of blend time for a VDB bioreactor design designated V18.

FIGS. 20A-20B illustrate a spatial analysis simulation of blend time for a VDB bioreactor design designated V17.

FIGS. 21A-21B illustrate a spatial analysis simulation of blend time for a VDB bioreactor design designated V16.

FIG. 28 provides a geometric representation of the VDB V5 with impeller design included in FIG. 10, a fluid velocity vector illustration similar to the V5 illustration included in FIG. 12 but with different rpm settings, and a fluid pathline illustration similar to the V5 illustration supplied by FIG. 11 but with different rpm settings.

FIG. 29 provides a geometric representation of the VDB V6 with impeller design included in FIG. 6, a fluid velocity vector illustration similar to the V6 illustration included in FIG. 7 but with different rpm settings, and a fluid pathline illustration similar to the V6 illustration also supplied by FIG. 7 but with different rpm settings.

DESCRIPTION OF THE INVENTION

Key concepts of the invention, as well as the purpose and operation of the invention including technical characteristics, will now be identified. Using a conical bottomed tank with continuous agitation, an aspect ratio of greater than 1:1

(liquid height to vessel diameter at liquid level) can be maintained to support minimal inoculation volume with sufficient liquid head for oxygen transfer during bulk up to larger scale. The culture volume is then bulked up through addition of media to sustain logarithmic growth via the continuous agitation design concept.

Initial VDB designs consisted of using multiple impellers of conventional design (i.e. the same types of impellers used in conventional bioreactors), but altering their size, number, and overall placement. CFD simulations of these designs indicated that an unacceptably large number of impellers (five or more) would be required in order to avoid separated fluid mixing zones and achieve adequate overall fluid mixing. Optimization of impeller type and size using four impellers resulted in blend times of approximately 200 to 400 seconds for a 20,000 liter fill VDB compared to approximately 60 seconds for a 20,000 liter conventional bioreactor. VDB designs were shifted to use largely a novel continuous agitator that runs nearly the entire vertical length of the reactor and provide more consistent agitation as a function of height. Numerous design changes of impeller pitch and blade number as well as baffle size resulted in blend times of approximately 68-100 seconds for a 20,000 liter fill VDB compared to approximately 60 seconds for a 20,000 liter conventional bioreactor.

FIG. 1 shows schematically (A) a 20,000 liter conventional bioreactor, (B and C) a 20,000 liter VDB with multiple conventional impellers, and (D) a 20,000 liter VDB with a continuous agitator.

The impellers for the VDB in FIG. 1B are sized and placed according to industry best practices. The impellers in FIG. 1C have been optimized to reduce mixing time at the same P/V value compared to FIG. 1B.

FIGS. 2A-2D show fluid velocity vectors from computational dynamics (CFD) simulations for a vertical cross section for each of the bioreactors operated at a similar average power/volume. FIGS. 2A-2C show four conventional impellers in a VDB result in detached mixing zones rather than single, connected fluid flow seen in the conventional bioreactor. FIG. 2D shows that these detached mixing zones are greatly reduced with the continuous agitator design.

Figure 3:
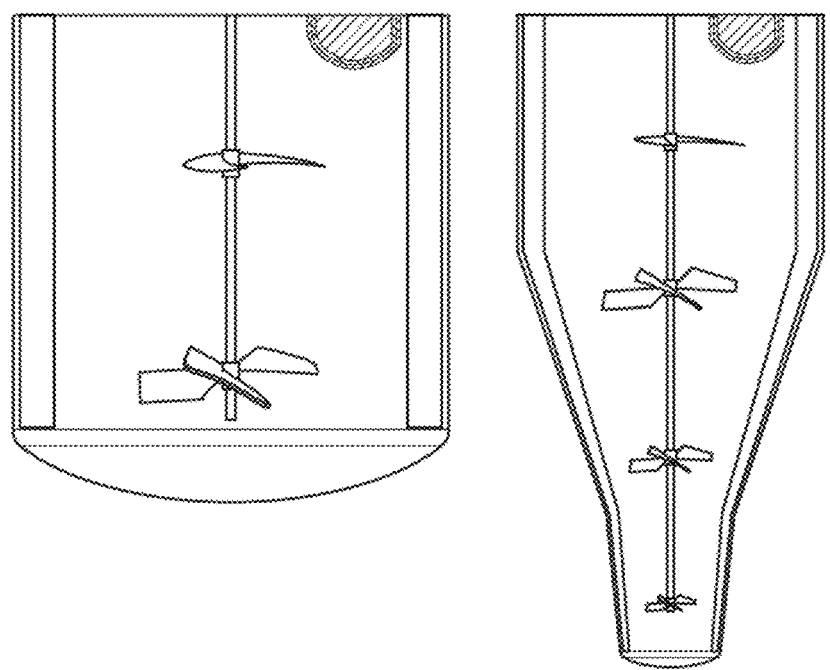
FIG. 3 illustrates an initial position of a tracer added to a conventional bioreactor and a VDB for computational fluid dynamics (CFD) simulations of mixing time.

CFD simulations of fluid mixing times were conducted. Mixing time is quantitatively defined as the time required for all points in the bioreactor to be within +/−5% of the final, mean value for an added tracer fluid. For these simulations, tracer fluid was added as a single bolus to the top of each bioreactor as shown in FIG. 3 and then the mixing of that bolus tracked as a function of time until uniformity was reached.

Figure 4A:
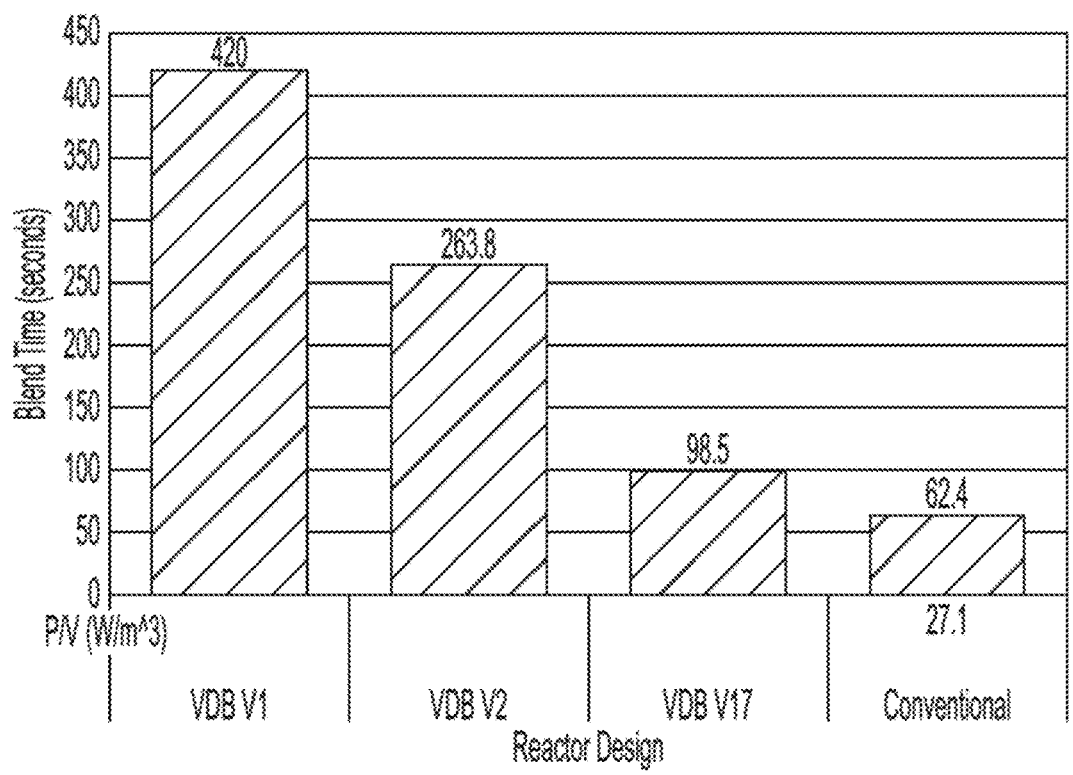
FIG. 4A supplies a comparison of calculated blend times from CFD simulations for certain configurations of the present invention, although the analysis had a geometrical issue that was fixed and adjusted in subsequent updates.
Figure 6:
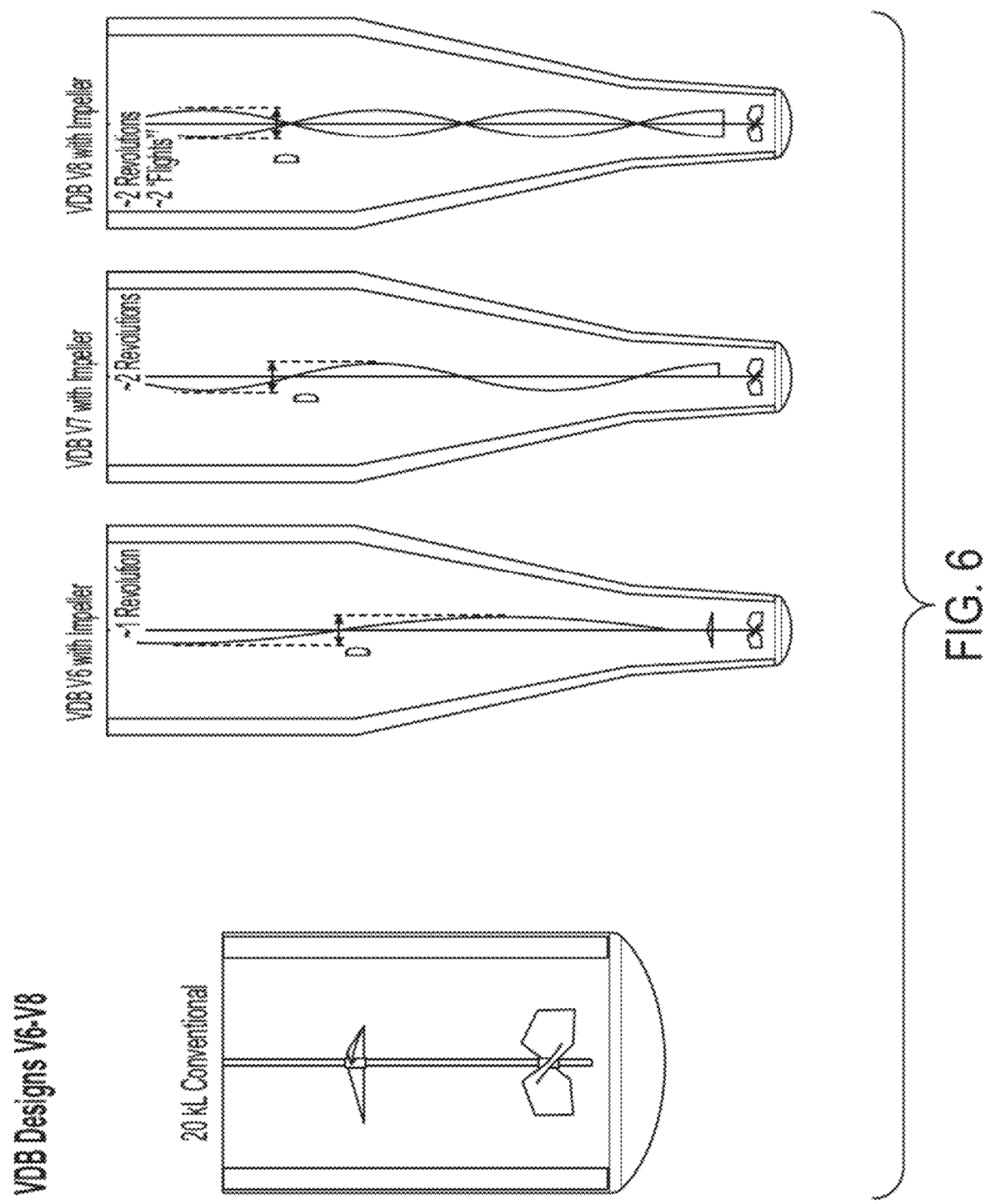
FIG. 6 supplies a comparison of a 20 kl conventional bioreactor and three VDB bioreactor designs designated V6, V7, and V8.
Figure 7:
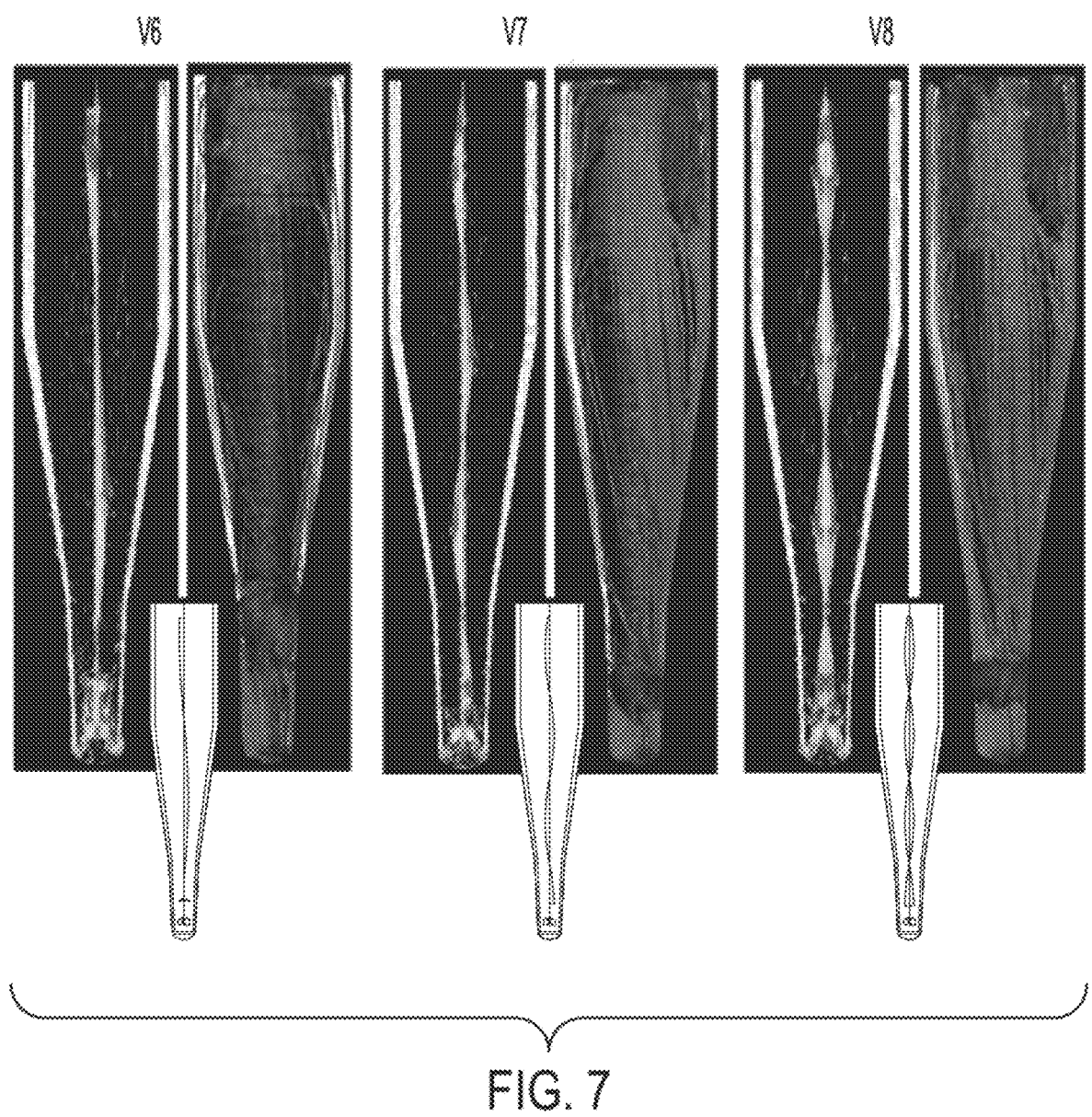
FIG. 7 supplies a comparison of a fluid velocity vectors and fluid pathlines for the VDB bioreactor designs designated V6, V7, and V8 mentioned.
Figure 9:
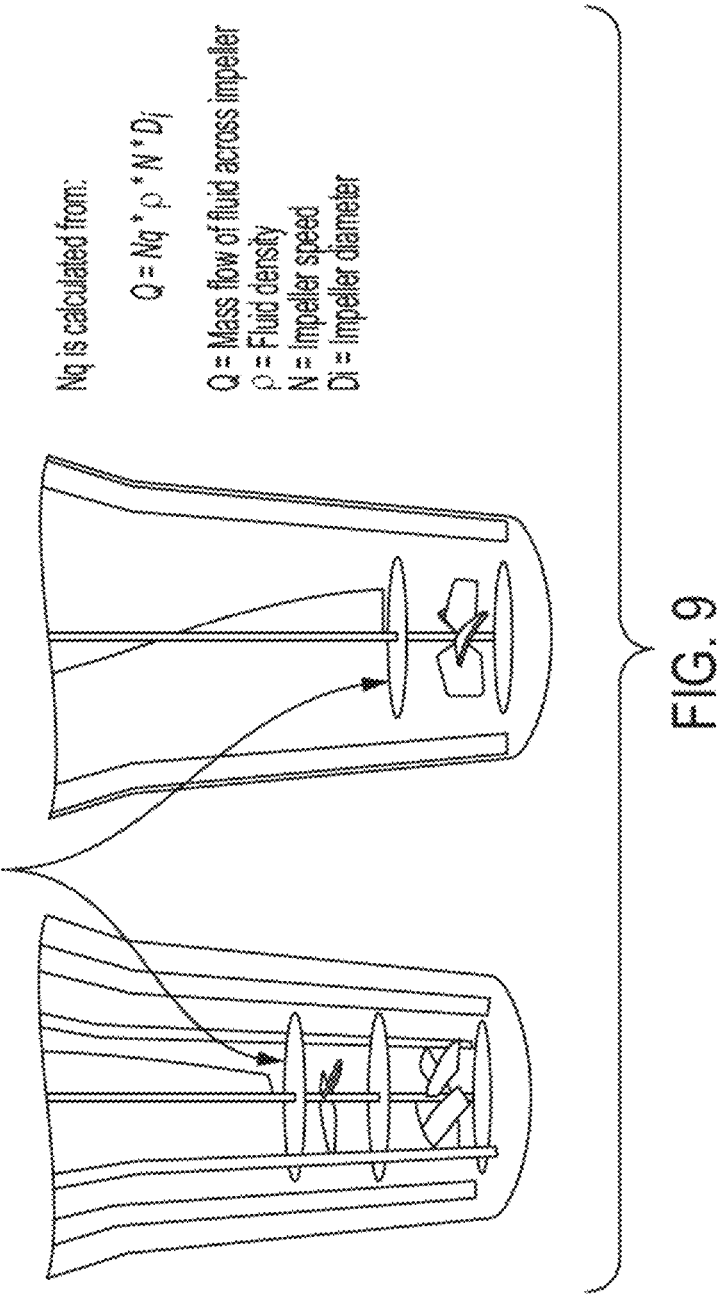
FIG. 9 supplies an example of flow number calculation.
Figure 10:
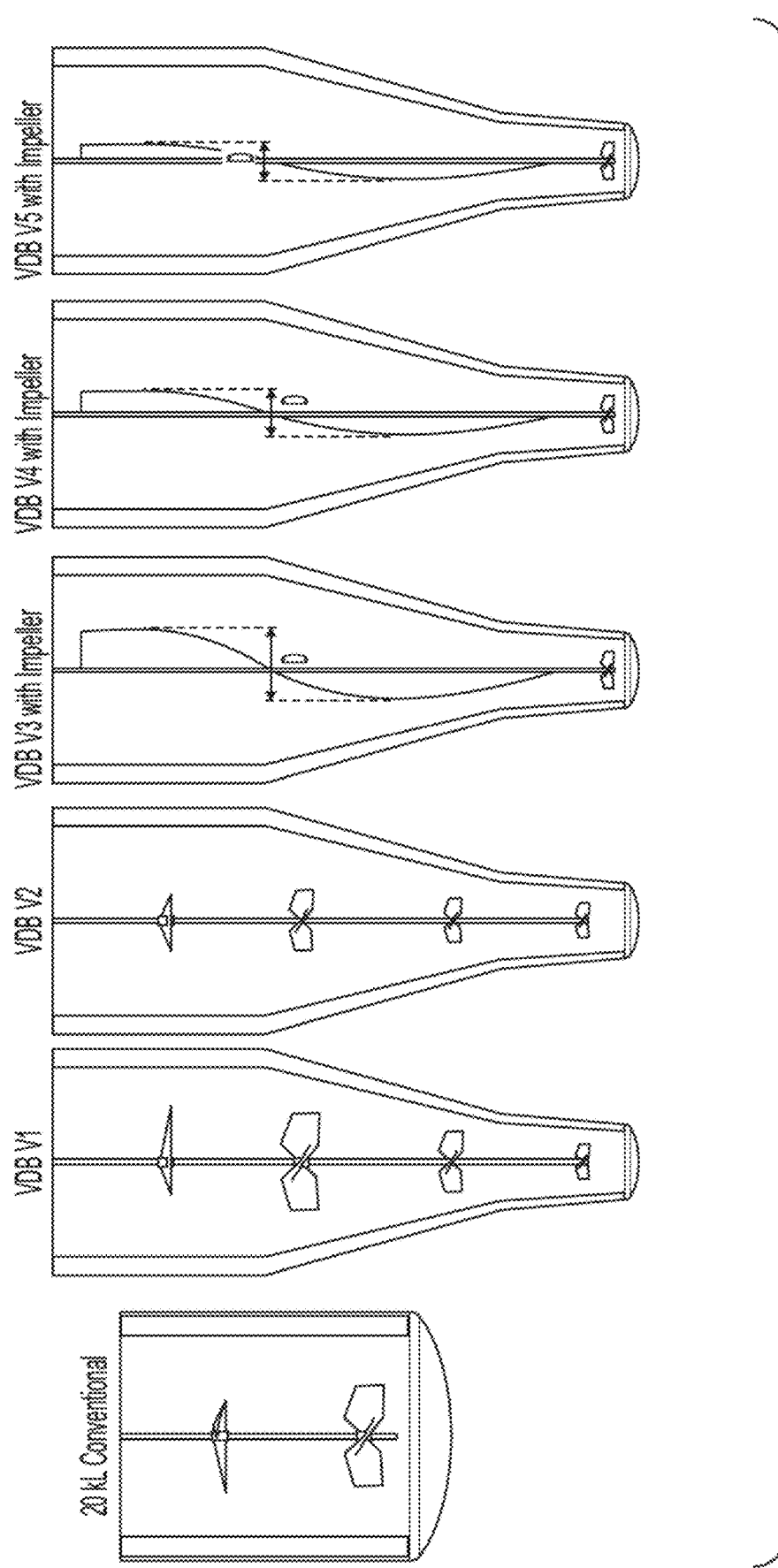
FIG. 10 supplies a comparison of a 20 kl conventional bioreactor and five VDB bioreactor designs designated V1, V2, V3, V4, and V5.
Figure 11:
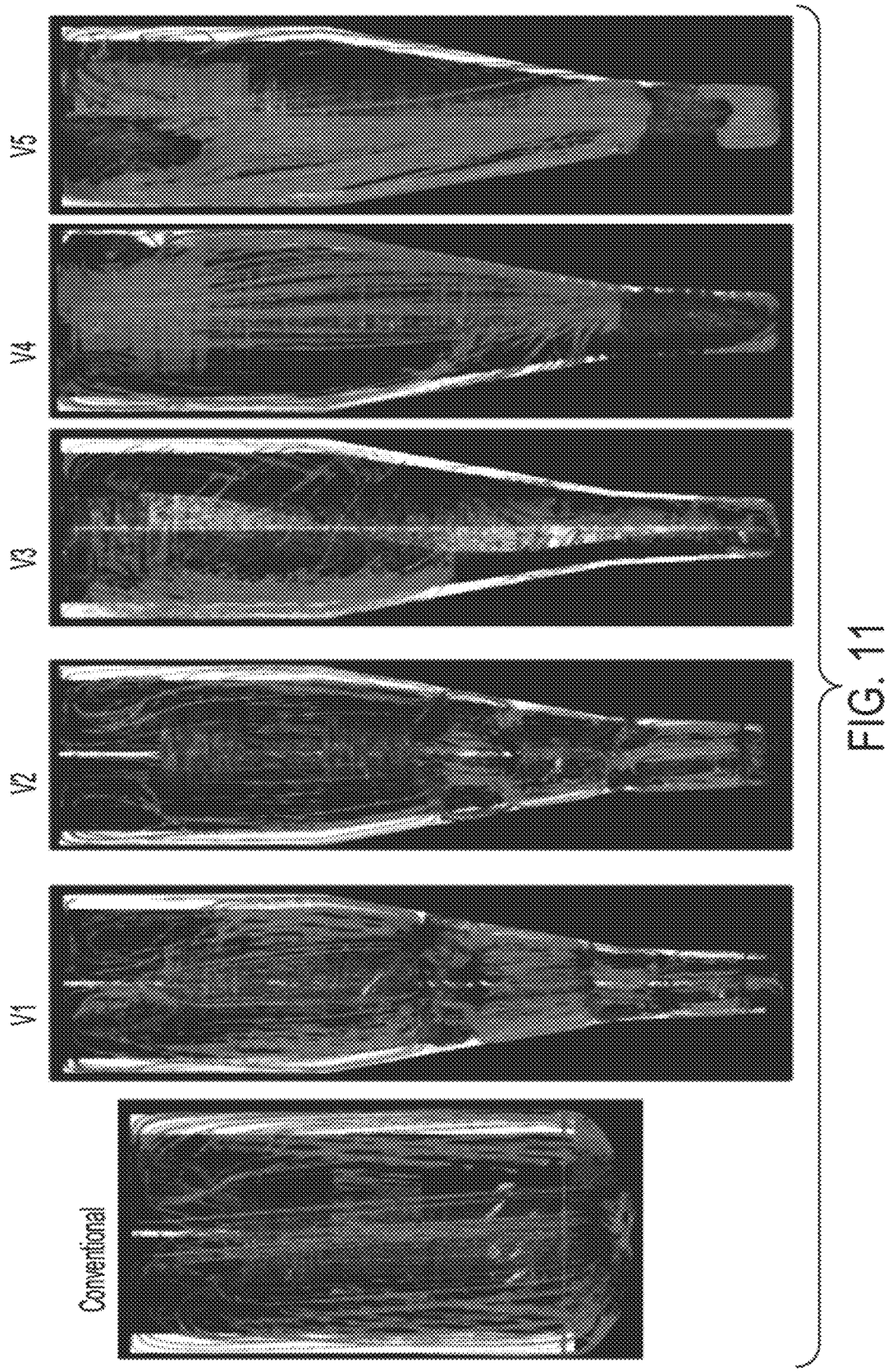
FIG. 11 supplies a comparison of fluid pathlines for the 20 kl conventional bioreactor and 20 kl VDB bioreactor designs designated V1, V2, V3, V4, and V5 mentioned.
Figure 12:
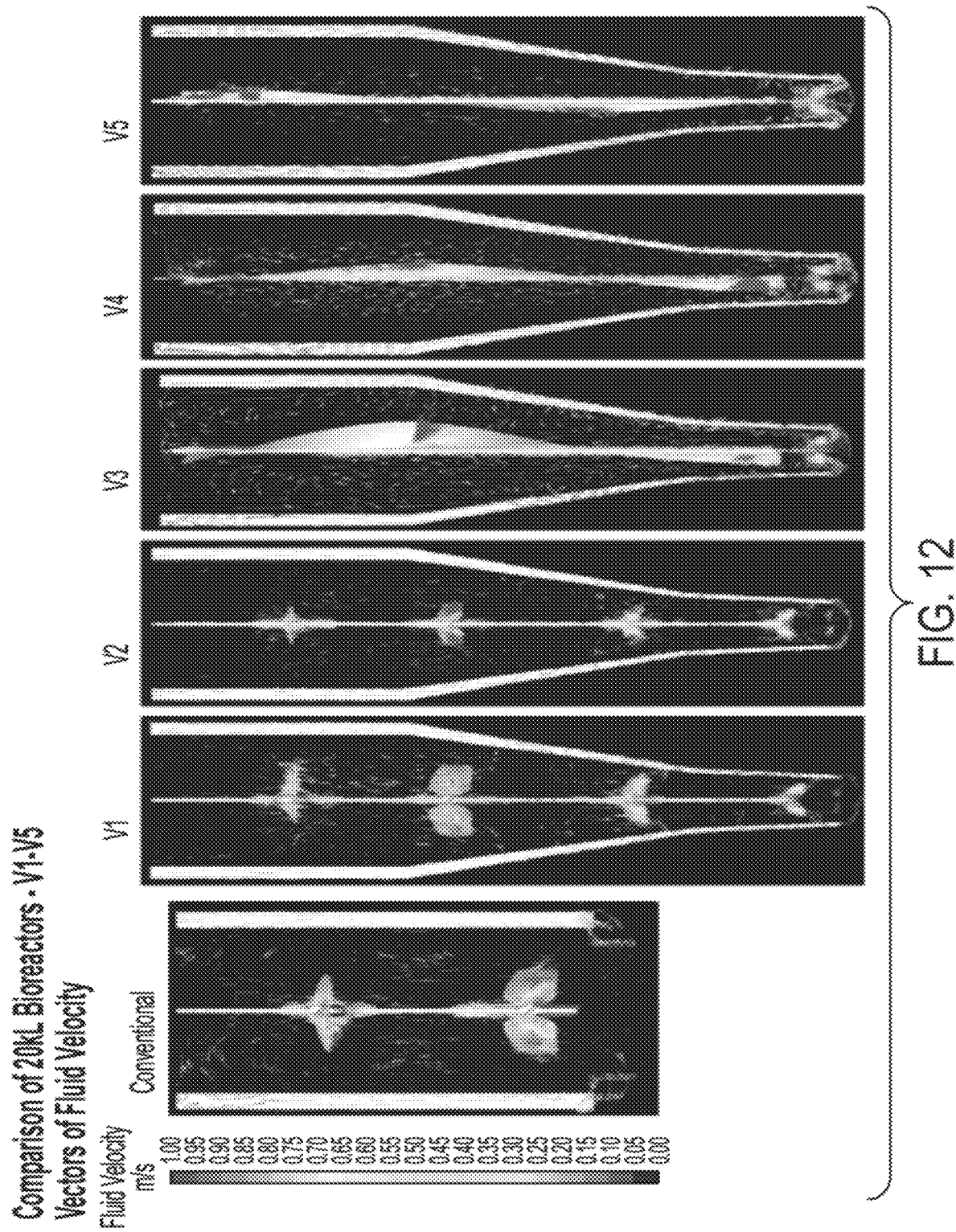
FIG. 12 is an illustration of fluid velocity vectors for the 20 kl conventional bioreactor and the 20 kl VDB bioreactor designs designated V1, V2, V3, V4, and V5 mentioned.

Results of these simulations are shown in FIGS. 4A and 4B, with FIG. 4B including a currently optimal Design V20. Blend time (as defined previously) for a VDB with 4 conventional impellers (Design V1) range from 420 seconds (using impellers sized using industry best practices) to 264 seconds (for impellers optimized to maximize fluid mixing—Design V2). These results suggest that greater than four impellers are likely needed to achieve acceptable mixing relative to a conventional bioreactor. Blend time for a VDB with a continuous agitator (Design V20) shows a blend time of about 100 seconds, indicating a significant improvement in mixing relative to the same VDB bioreactor with conventional impellers.

Figure 14A:
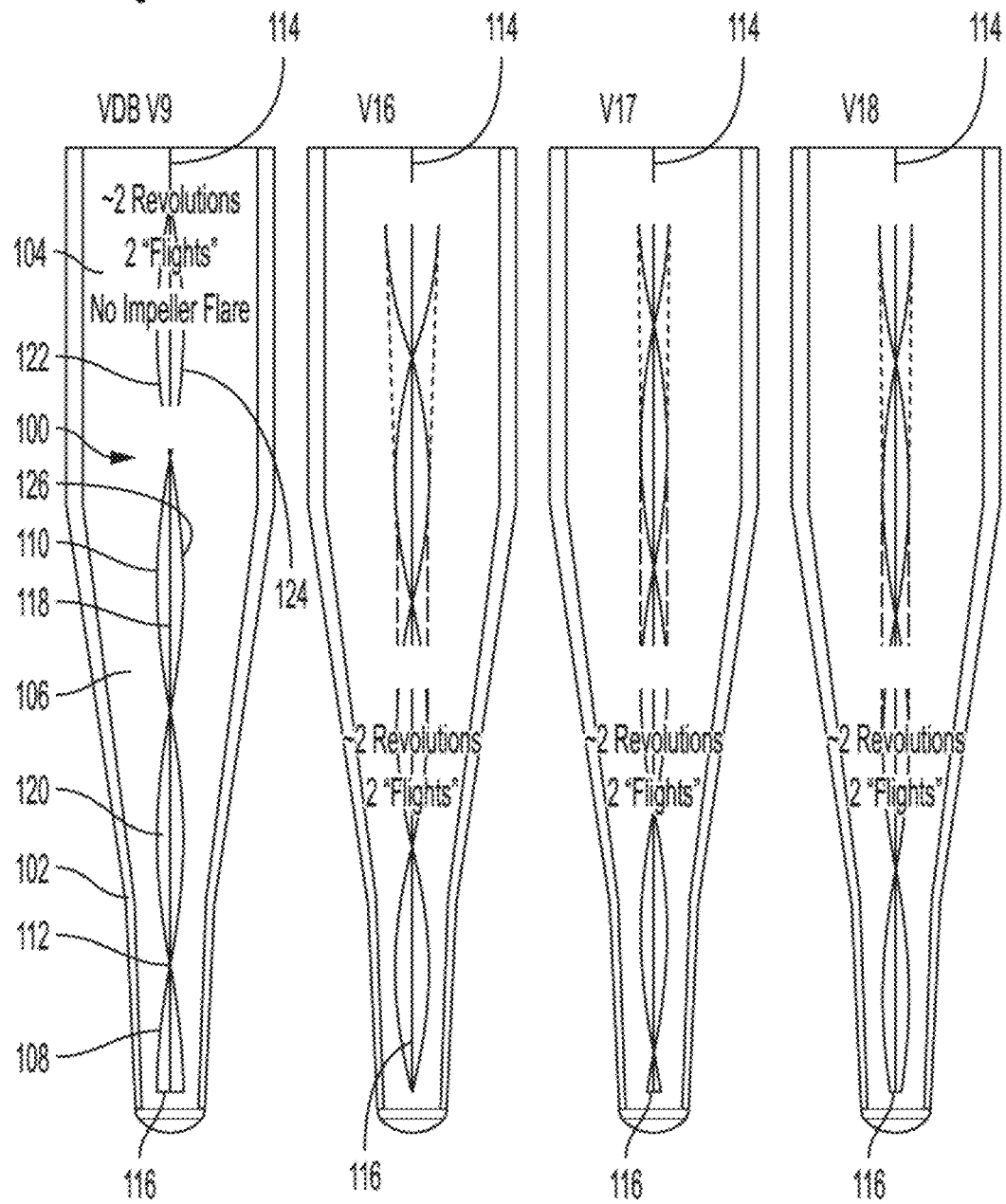
FIGS. 14A-14B provide schematic representations of axial distribution of mixing energy at an equal power to volume ratio for VDB bioreactor designs designated V9, V16, V17, and V18.

The particular illustrations supplied by FIGS. 14A-16 show what are presently considered to be optimal designs. Referring by way of example to FIGS. 14A-14B, each of the impeller configurations shown is suitable for use in multiple vessel section VDBs such as those disclosed by the Mietzner et al. '828 A1 publication referred to above. As shown in FIG. 14A, an impeller 100 is usable in a variable diameter bioreactor 102 having multiple vessel sections 104, 106, and 108 of successively increasing or decreasing volume. The impeller 100 illustrated includes an impeller blade 110 extending along an impeller blade axis 112 between first and second axial ends 114, 116 and having opposed impeller blade faces 118, 120, an impeller blade leading edge 122, and an impeller blade trailing edge 124. As illustrated, the leading and trailing edges 122 and 124 each define a helix or spiral between the first and second axial ends 114, 116 of the impeller blade 110.

Figure 14B:
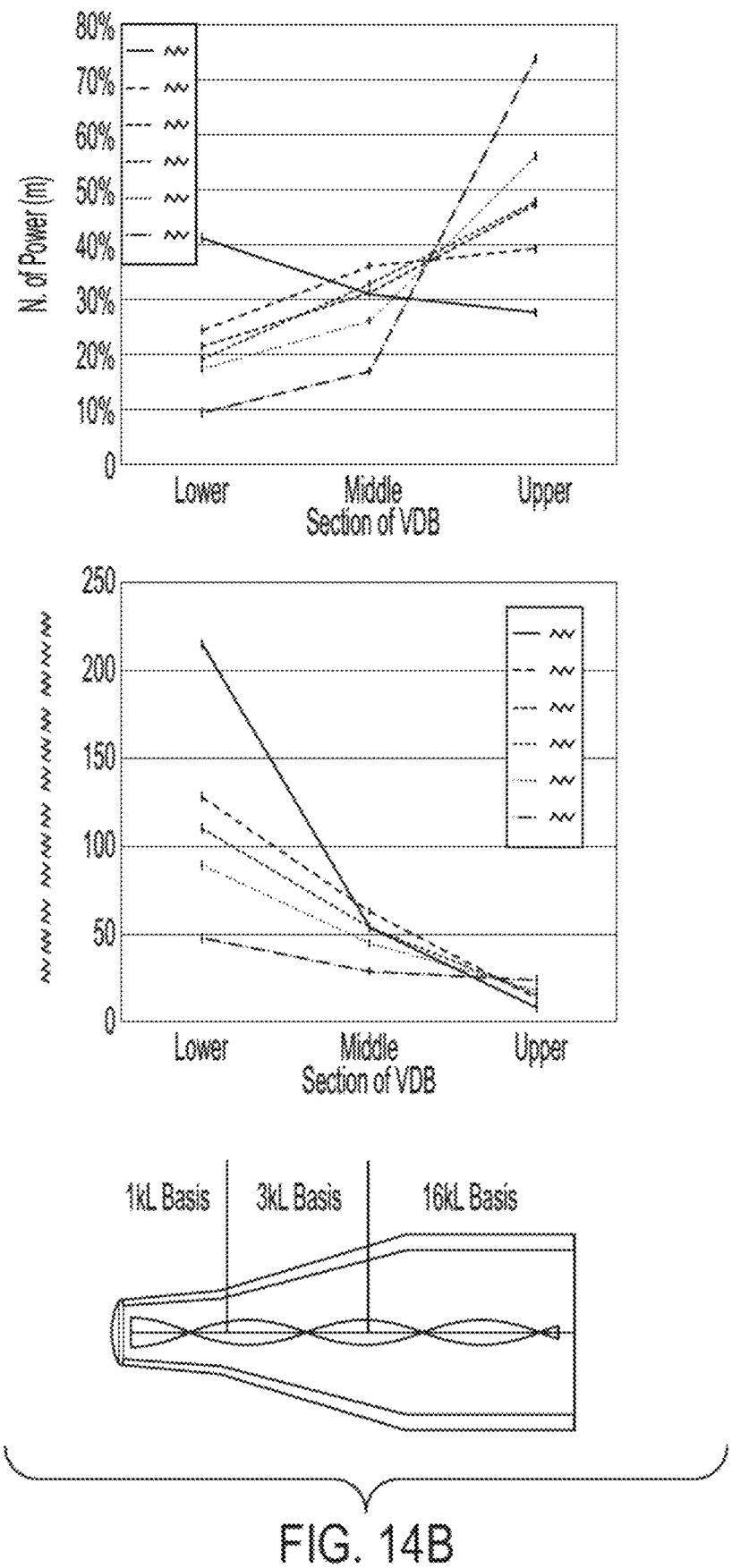
Figure 15:
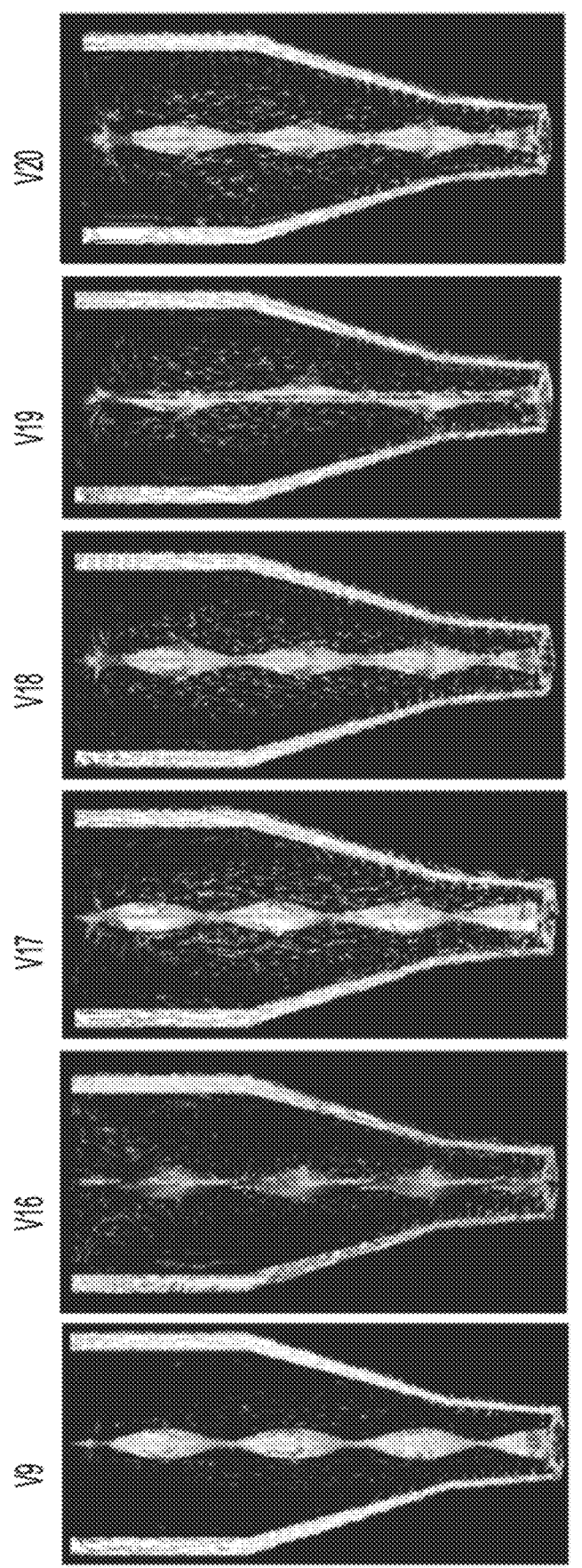
FIG. 15 is a schematic representation of fluid velocity vectors at an equal pressure to volume ratio for VDB bioreactor designs designated V9, V16, V17, V18, V19, and V20.
Figure 16:
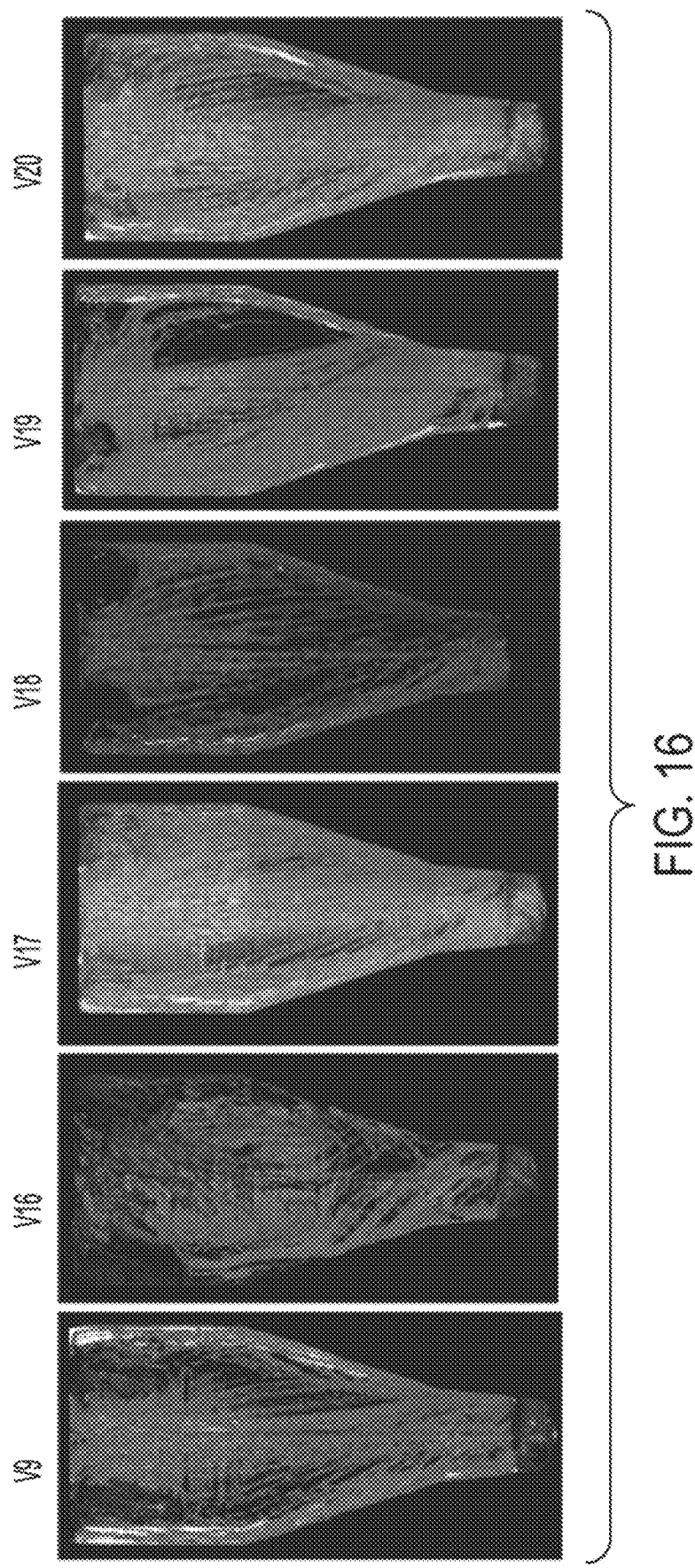
FIG. 16 supplies a comparison of fluid pathlines for the VDB bioreactor designs designated V9, V16, V17, V18, V19, and V20 mentioned.
Figure 18A:
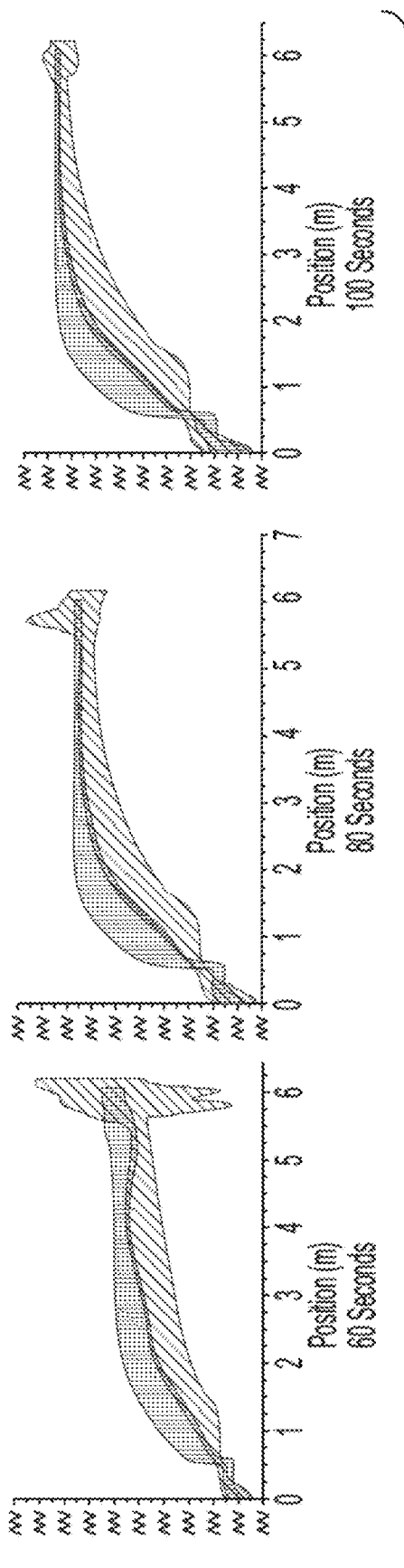
Figure 20B:
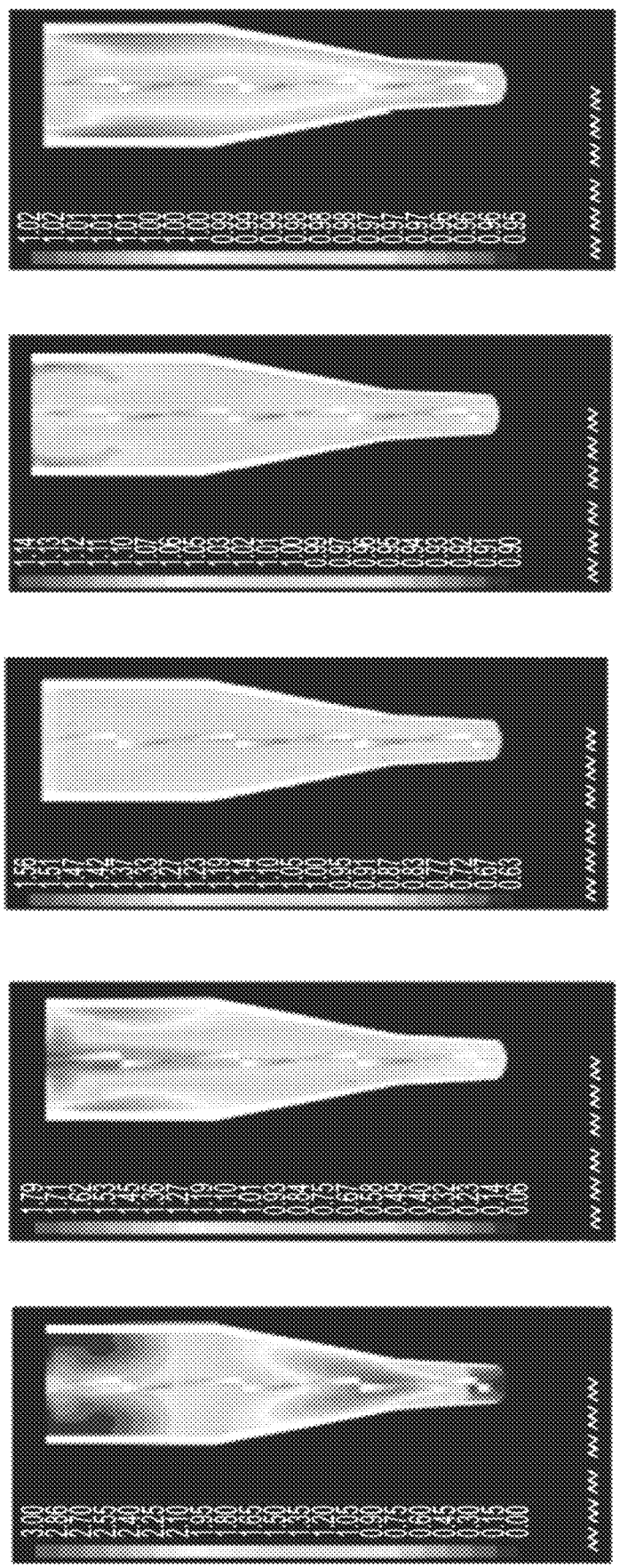
Figure 22:
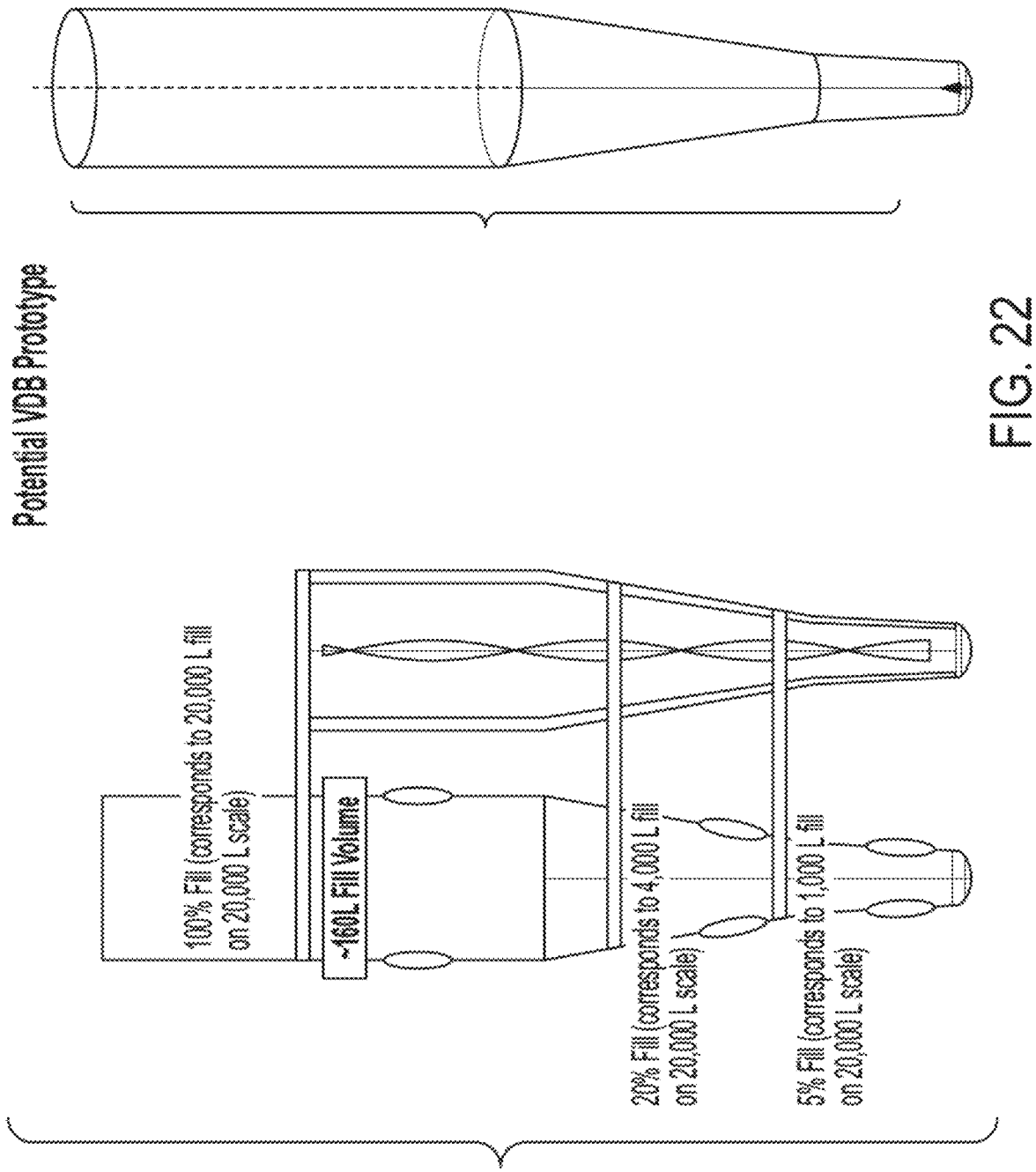
FIG. 22 illustrates the configuration of a potential VDB prototype.
Figure 23:
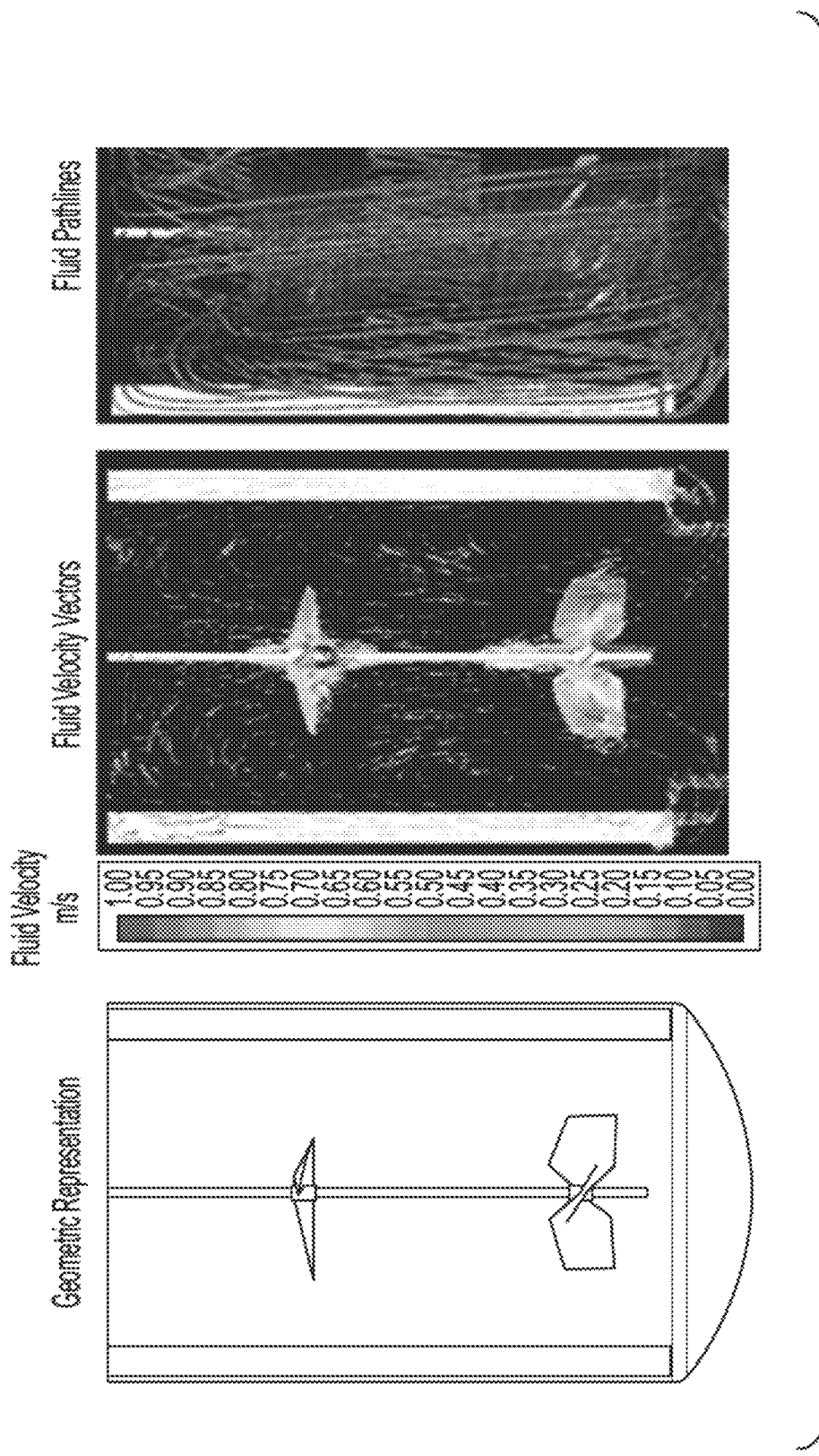
FIG. 23 provides views of a conventional 20,000 liter bioreactor, including a geometric representation similar to FIG. 1A, a fluid velocity vector representation similar to FIG. 2A but with different rpm settings, and a fluid pathline representation similar to those of FIGS. 7, 11, and 16 but at with different rpm settings.
Figure 24:
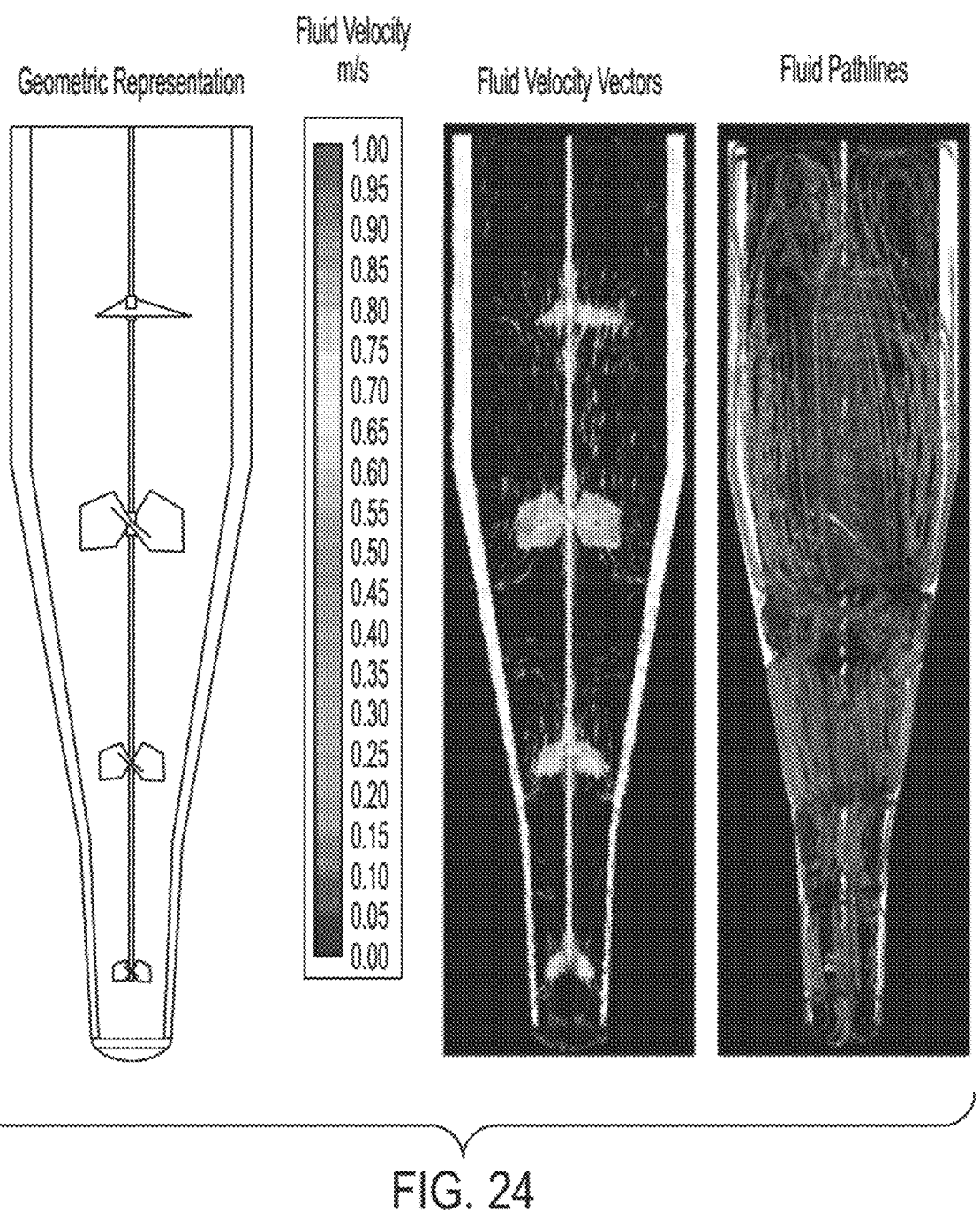
FIG. 24 provides a geometric representation of the VDB V1 design included in FIG. 10, a fluid velocity vector illustration similar to the V1 illustration included in FIG. 12, and a fluid pathline illustration similar to the V1 illustration supplied by FIG. 11 but with different rpm settings.
Figure 25:
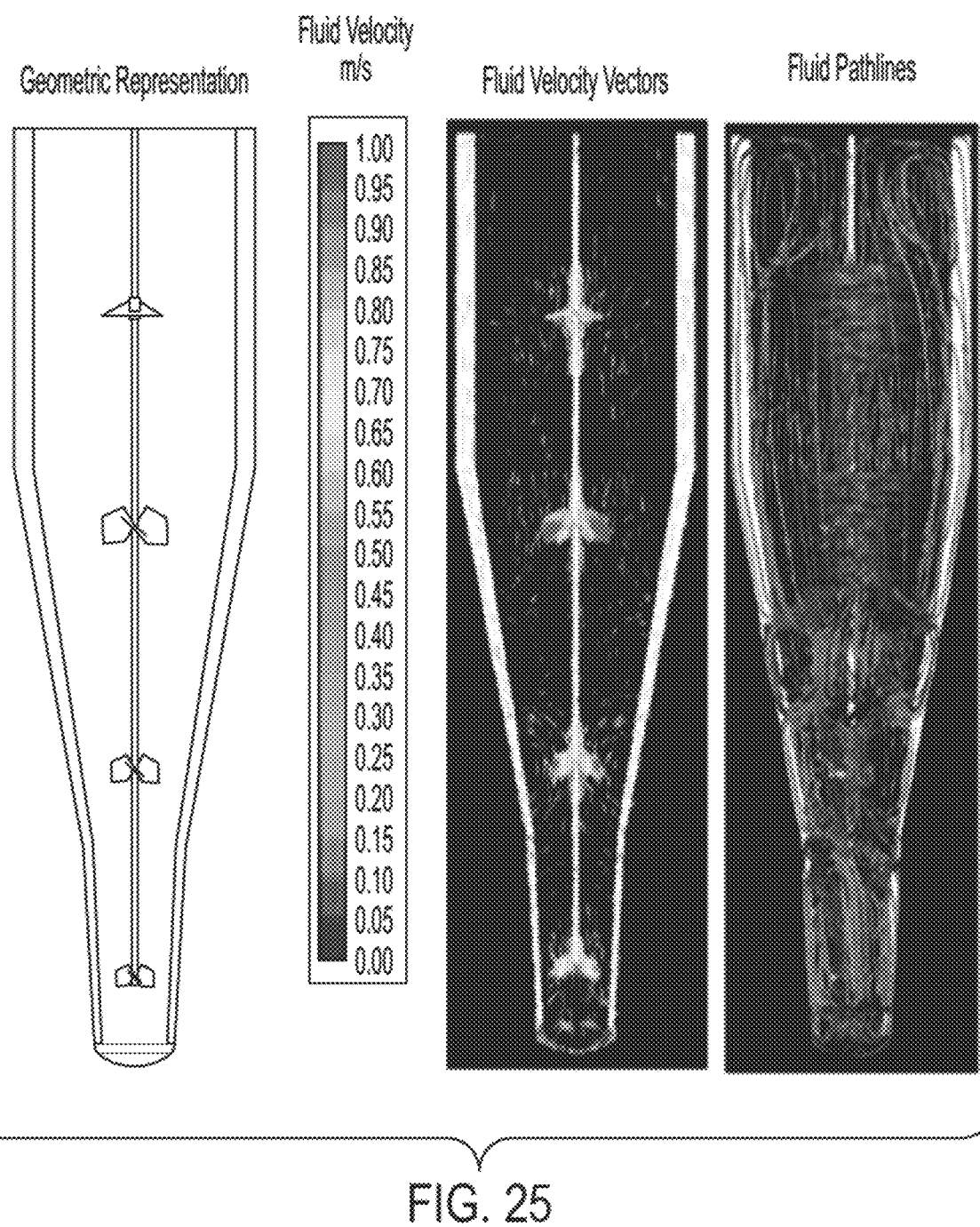
FIG. 25 provides a geometric representation of the VDB V2 design included in FIG. 10 but with different rpm settings, a fluid velocity vector illustration similar to the V2 illustration included in FIG. 12 but with different rpm settings, and a fluid pathline illustration similar to the V2 75 rpm illustration supplied by FIG. 11 but with different rpm settings.
Figure 26:
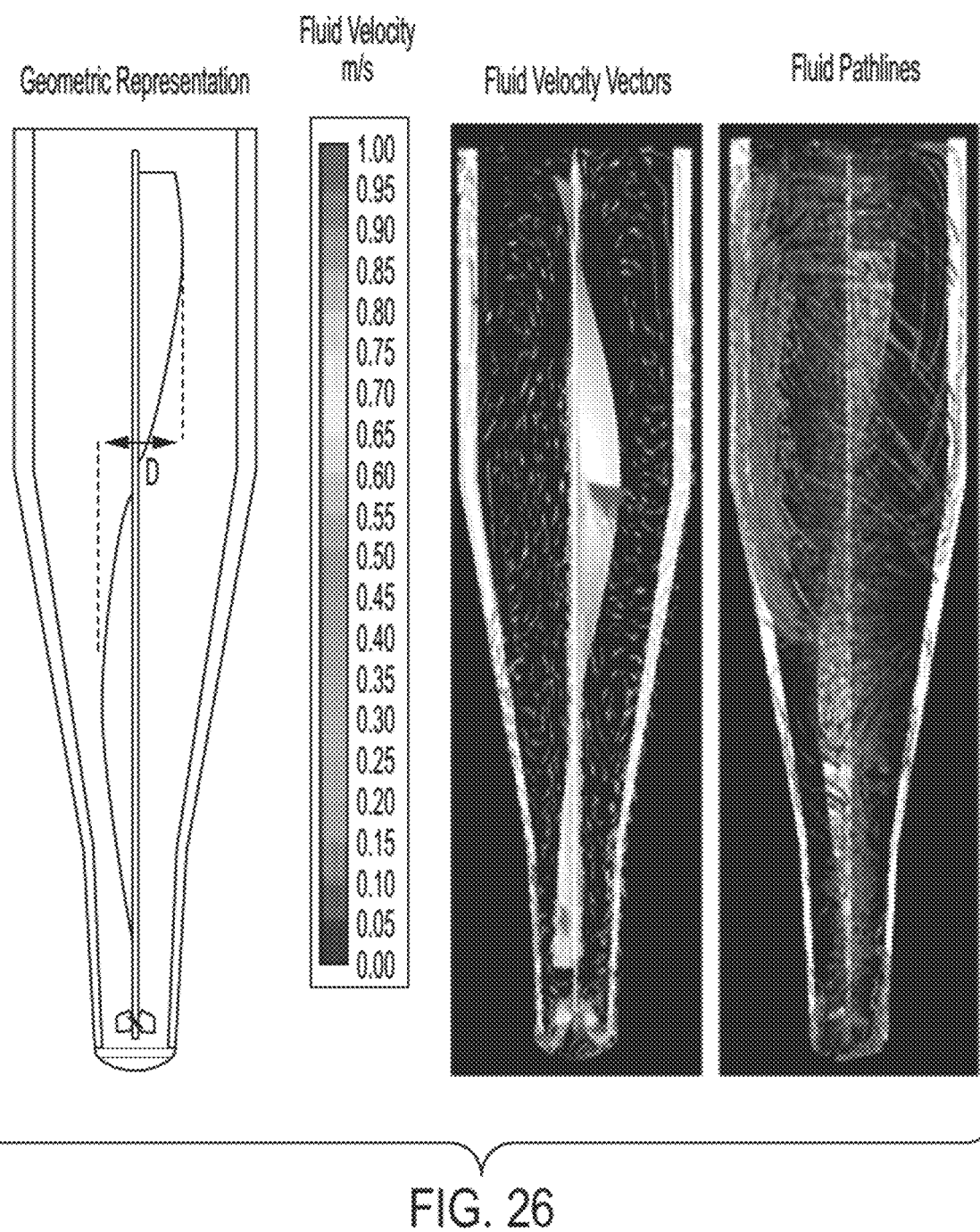
FIG. 26 provides a geometric representation of the VDB V3 with impeller design included in FIG. 10, a fluid velocity vector illustration similar to the V3 illustration included in FIG. 12 but with different rpm settings, and a fluid pathline illustration similar to the V3 illustration supplied by FIG. 11 but with different rpm settings.
Figure 27:
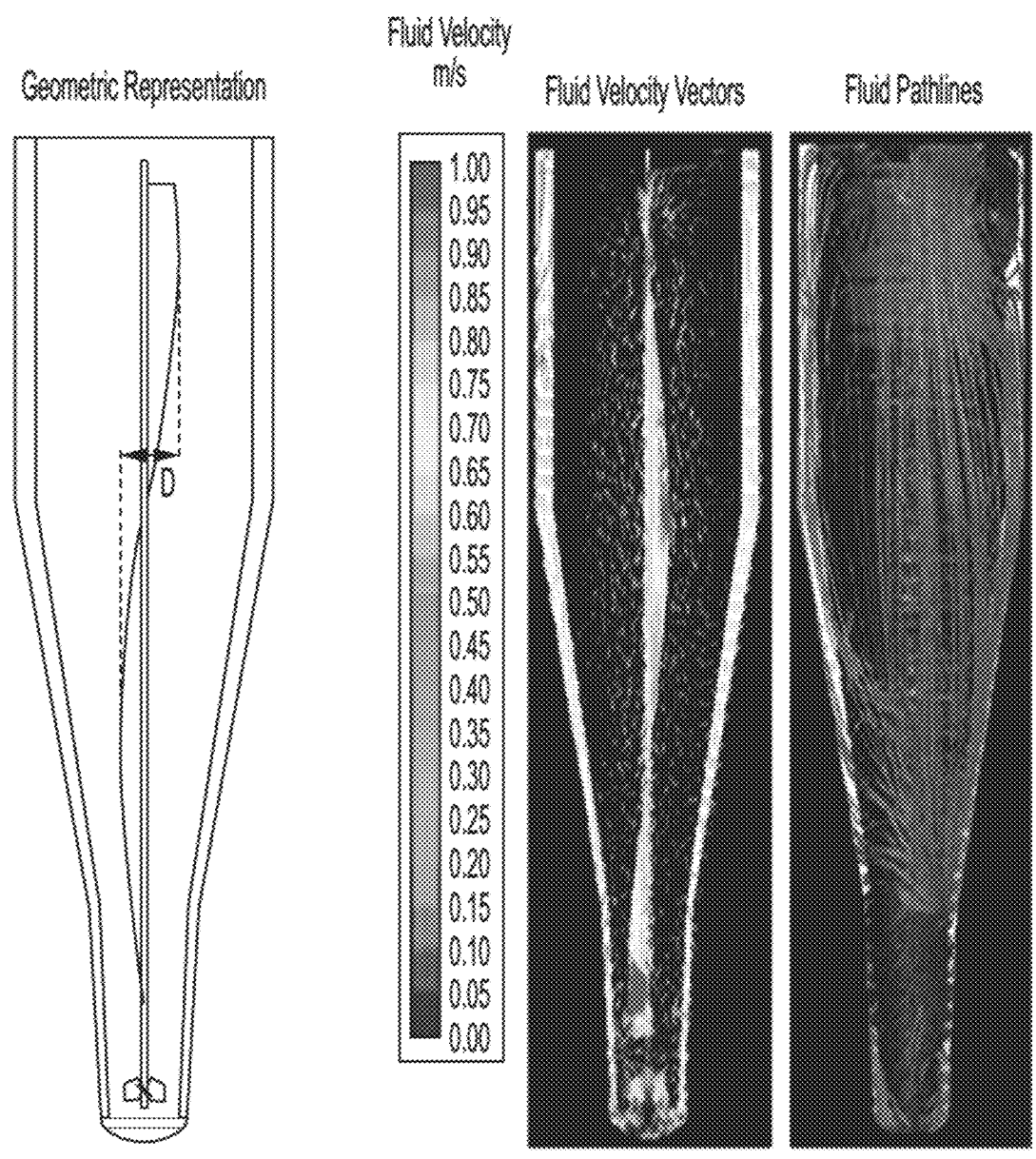
FIG. 27 provides a geometric representation of the VDB V4 with impeller design included in FIG. 10, a fluid velocity vector illustration similar to the V4 46 rpm illustration included in FIG. 12, and a fluid pathline illustration similar to the V4 illustration supplied by FIG. 11 but with different rpm settings.
Figure 30:
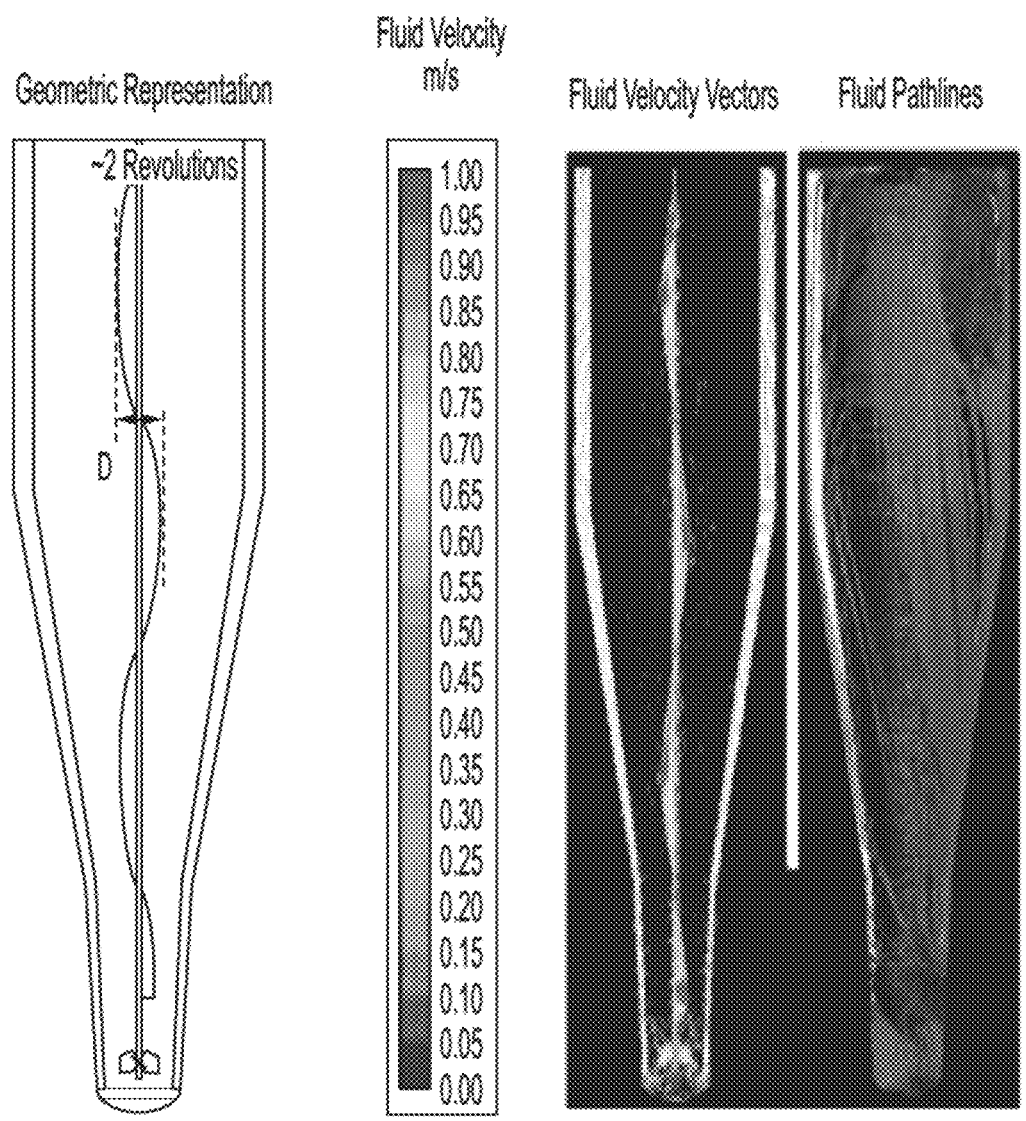
FIG. 30 provides a geometric representation of the VDB V7 with impeller design included in FIG. 6, a fluid velocity vector illustration similar to the V7 illustration included in FIG. 7 but with different rpm settings, and a fluid pathline illustration similar to the V7 illustration also supplied by FIG. 7 but with different rpm settings.
Figure 31:
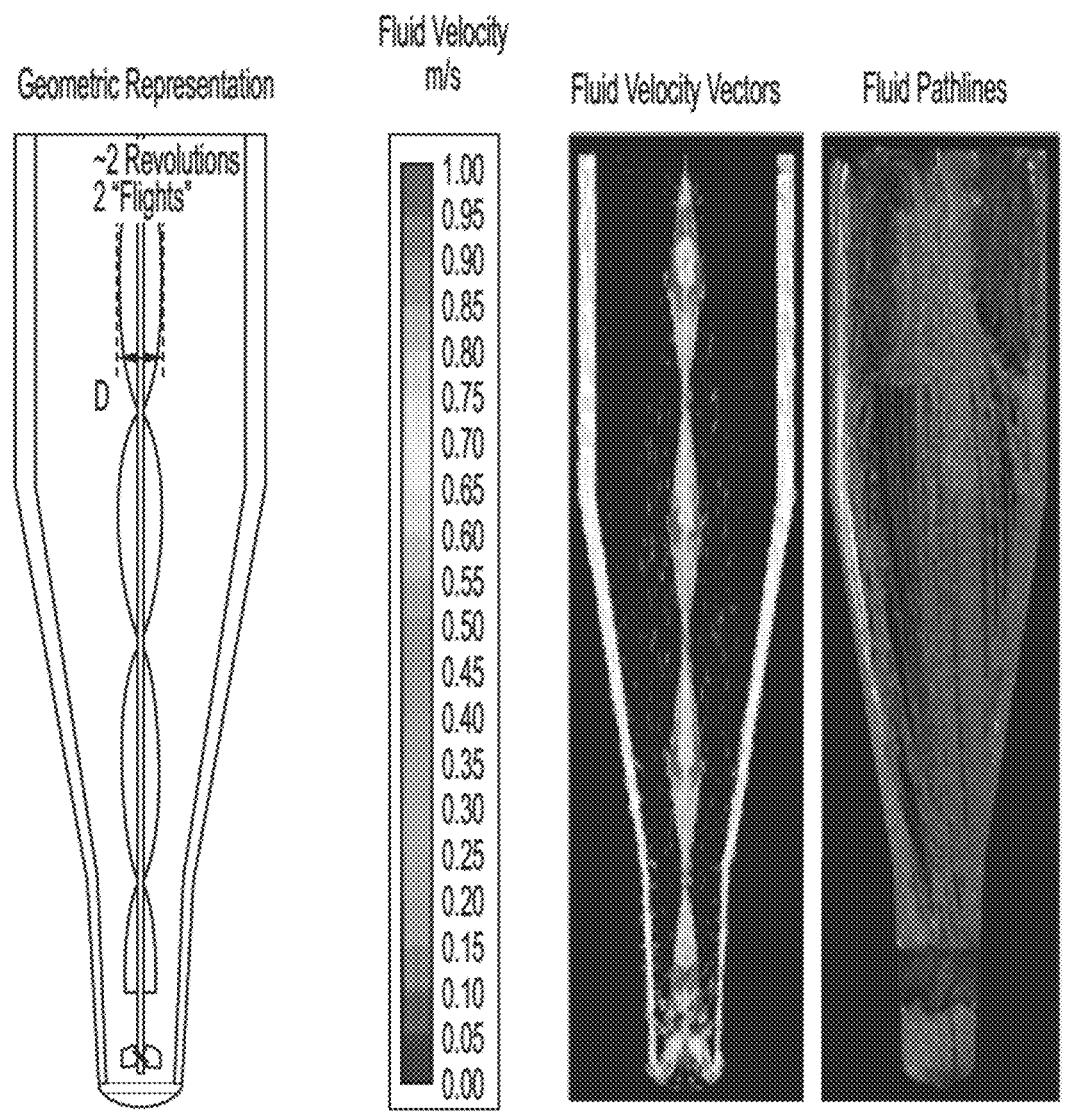
FIG. 31 provides a geometric representation of the VDB V8 with impeller design included in FIG. 6, a fluid velocity vector illustration similar to the V8 illustration included in FIG. 7 but with different rpm settings, and a fluid pathline illustration similar to the V8 illustration also supplied by FIG. 7 but with different rpm settings.
Figure 32:
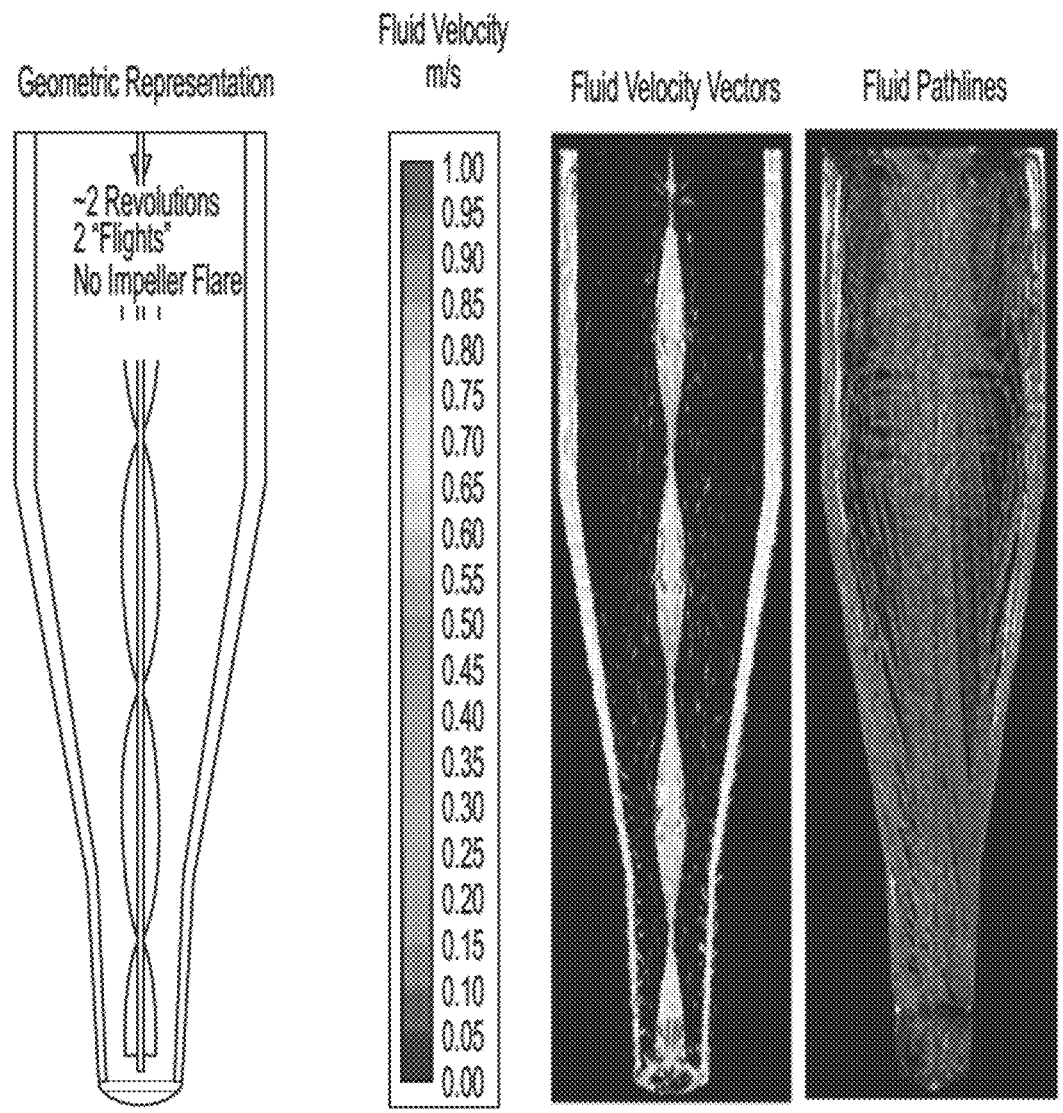
FIG. 32 provides a geometric representation of the VDB V9 design included in FIGS. 14A-14B but with different rpm settings, a fluid velocity vector illustration similar to the V9 illustration included in FIG. 15 but with different rpm settings, and a fluid pathline illustration similar to the V9 rpm illustration supplied by FIG. 16 but with different rpm settings.
Figure 33:
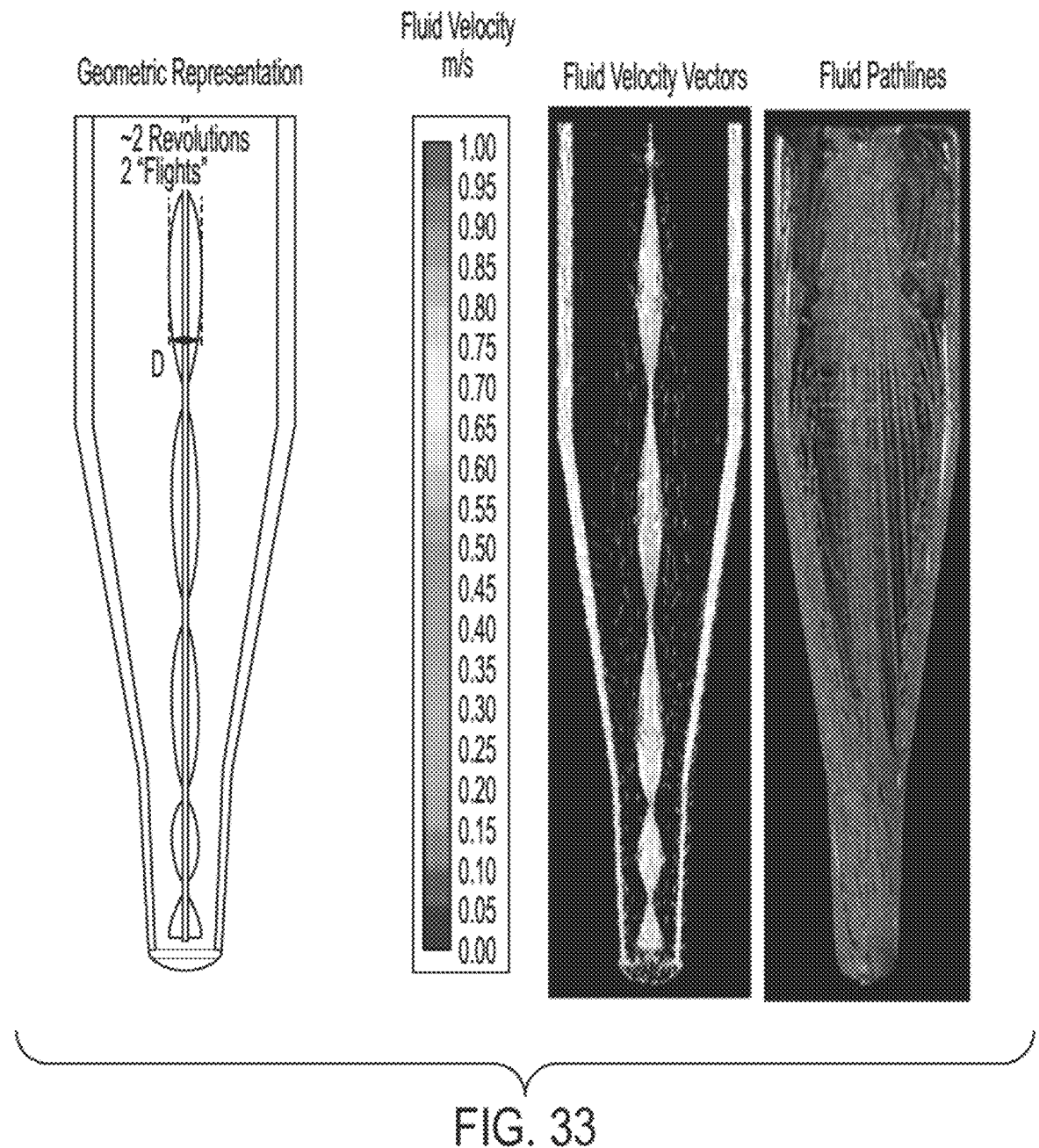
FIG. 33 provides a geometric representation of a further VDB bioreactor designs, designated VDB Design V10, a fluid velocity vector illustration for the VDB Design V10, and a fluid pathline illustration for the VDB Design V10.
Figure 34:
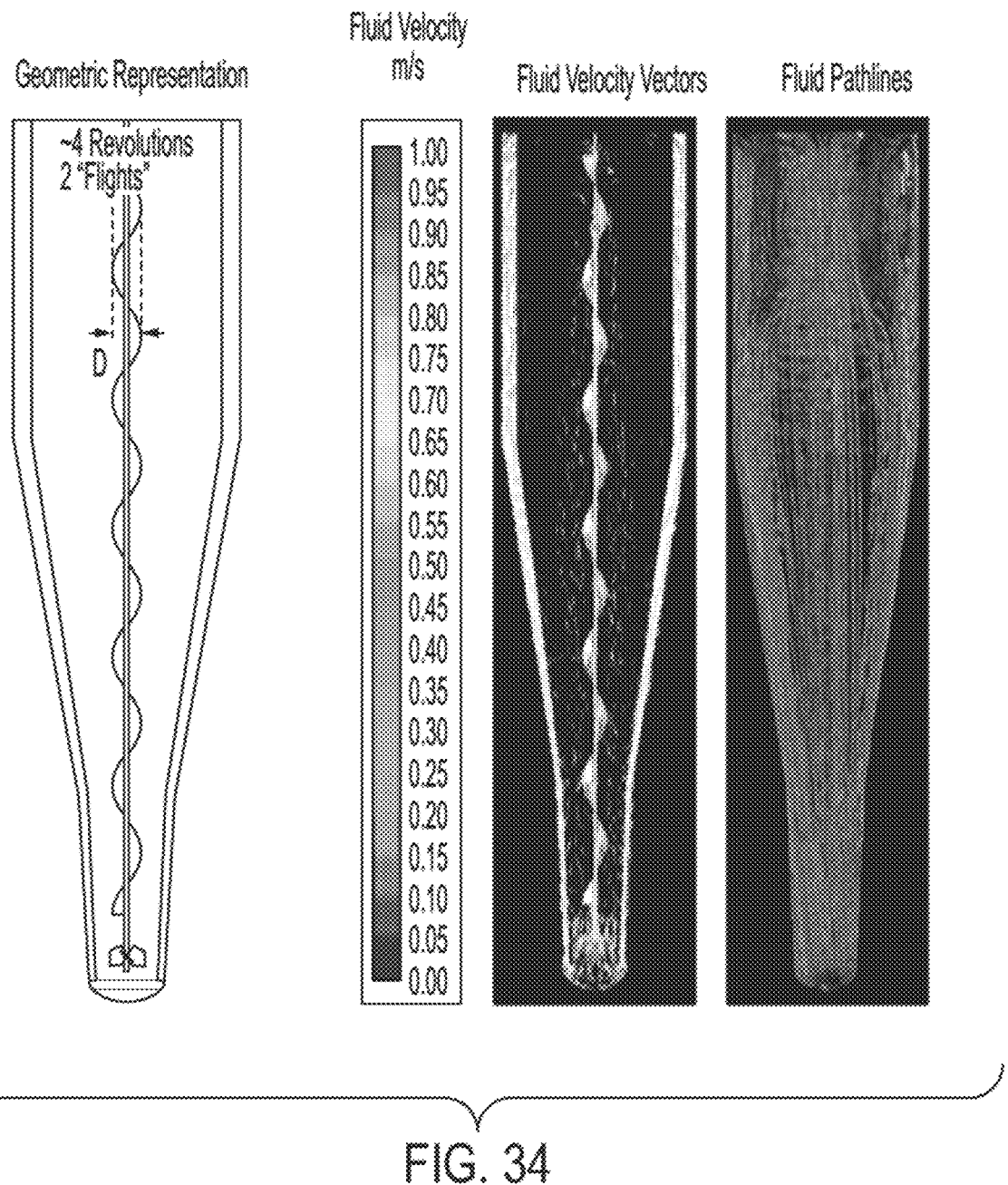
FIG. 34 provides a geometric representation of a further VDB bioreactor designs, designated VDB Design V11, a fluid velocity vector illustration for the VDB Design V11, and a fluid pathline illustration for the VDB Design V11.

In each arrangement shown in FIG. 14A-14B, the impeller blade 110 is one of at least two impeller blades 110, 126 joined together along an impeller shaft 118 extending axially along the impeller blade axis 112 mentioned. The helix or spiral has a pitch approximately equal to one half of a length between the first and second axial ends 114, 116; as illustrated in FIG. 14A, the pitch mentioned is one half of the length mentioned. Differences between the versions V9, V16, V17, and V18 shown in FIGS. 14A-14B reside primarily in the combined diameter of shaft 118 and widths of the blades 110 and 126, with the V9 combined diameter and widths being 0.35 m between the first and second axial ends 114, 116, the V16 combined diameter and widths tapering from 0.75 m at the first axial end 114 to 0.35 m at the second axial end 116, the V17 combined diameter and widths tapering from 0.45 m at the first axial end 114 to 0.35 m at the second axial end 116, and the V18 combined diameter and widths tapering from 0.50 m at the first axial end 114 to 0.35 m at the second axial end 116.

Features considered of the invention considered different (i.e. novel) when compared to the state of the art include the use of a continuous impeller alone or in conjunction with another impeller (twin shaft design) within a typical cylindrical bioreactor or in a Variable Diameter Bioreactor.

With respect to envisioned products, processes, or applications, the biggest benefit would be bioreactor systems for contract manufacturing. Ease of configuration for total production volume and minimized footprint are key attributes for this application (flexibility for low, mid, and high titer processes). Ease of modification of existing bioreactors with this agitator technology to eliminate seed train equipment (N-1 and possibly more).

It is clear from the present disclosure that a scaled down version could be fabricated and used for any desired mixing, mass transfer, and cleaning in place attributes. A scaled down version could be used to replace seed train and feed a production bioreactor (traditional or VDB).

The examples below are set out in the Mietzner et al. '828 A1 publication mentioned above, which is incorporated herein by reference, but these examples are explicitly included here as well for the sake of completeness.

Examples

The relationship between the volume, diameter and properties for cell growth of the variable diameter bioreactors of the present invention requires the consideration of many factors. The below equation provides a useful guide when designing bioreactors of the present invention:

Sphere: $V = \frac{\pi}{3} y^2 (1.5D - y)$

Cylinder: $V = \frac{LD^2}{8}(\theta - \sin(\theta)) \quad T = 2\sqrt{y(D-y)} = D\sin\left(\frac{\theta}{2}\right)$ Cone: $V = \frac{\pi h}{12}\left(D_{bot}^2 + D_{bot}D_{top} + D_{top}^2\right) \quad z = \frac{1}{2h}(D_{top} - D_{bot})$ For example, when designing the bioreactor of the present invention to work with volumes up to 20,000 L, the variable diameter bioreactor would have the following proportions:
Total Volume: 20,000 L
Cone Volume: 15,000 L
$Diameter_{top}$: 7 ft
$Diameter_{bottom}$: 3 ft
Total Height: 30.2 ft
Cylinder Volume: 5,000 L
Cone Height: 25.6 ft
Cylinder Height: 4.6 ft As another example, when designing the bioreactor of the present invention to fit into a certain space in a manufacturing facility or the like, where the height is limited to twenty feet, the above equation would yield the following proportions:
Total Volume: 16,458 L
Cone Volume: 9,341 L
$Diameter_{top}$: 8 ft
$Diameter_{bottom}$: 2 ft
Total Height: 20 ft
Cylinder Volume: 7,117 L
Cone Height: 15 ft
Cylinder Height: 5 ft The above example can have four impellers.

As another example, the design of the present invention allows variable diameter bioreactors to be built in excess of 20,000 L, which is new to the art. Specifically, a variable diameter bioreactor could be built with the following proportions:
Total Volume: 25,000 L
Cone Volume: 15.000 L
$Diameter_{top}$: 7.9 ft
$Diameter_{bottom}$: 2.5 ft
Total Height: 30 ft
Cylinder Volume: 10,000 L
Cone Height: 22.8 ft
Cylinder Height: 7.2 ft Unless described otherwise above, the above description may be further understood as follows. The devices, facilities and methods described herein are suitable for use in and with culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesized by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Patent Application Publication Nos. 2012/0077429; and 2009/0305626; and U.S. Pat. Nos. 9,388,373, 8,771, 635, 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina,* or *Ochromonas*), or a plant cell (e.g., cells from monocotyledonous plants (e.g., maize, rice, wheat, or Setaria), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto,* or *B. megaterium.* In embodiments, the cell is *B. subtilis,* such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus, Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CIVIL vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S pneumoniae pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table A of US 2016/0097074:

TABLE A

| Protein Product | Reference Listed Drug |
| --- | --- |
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |

TABLE A-continued

| Protein Product | Reference Listed Drug |
| --- | --- |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/ Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/ Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |

TABLE A-continued

| Protein Product | Reference Listed Drug |
|---|---|
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone Antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2*a* | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive™ (Serostim ®) |

In embodiments, the polypeptide is a hormone, blood clotting/coagulation factor, cytokine/growth factor, antibody molecule, fusion protein, protein vaccine, or peptide as shown in Table B.

TABLE B

| Therapeutic Product type | Product | Trade Name |
|---|---|---|
| Hormone | Erythropoietin, Epoein-α Darbepoetin-α | Epogen, Procrit Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel Luveris |
| | Lutropin-α | GlcaGen |
| | Glucagon | Geref |
| | Growth hormone releasing hormone (GHRH) | ChiRhoStim (human peptide), SecreFlo (porcine peptide) |
| | Secretin | |
| | Thyroid stimulating hormone (TSH), thyrotropin | Thyrogen |
| Blood Clotting/ Coagulation Factors | Factor VIIa | NovoSeven |
| | Factor VIII | Bioclate, Helixate, Kogenate, Recombinate, ReFacto |
| | Factor IX | |
| | Antithrombin III (AT-III) | Benefix |
| | Protein C concentrate | Thrombate III Ceprotin |
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table C.

TABLE C

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T cells (Barbara Ann Karmanos Cancer Institute) | T-cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |

TABLE C-continued

Bispecific Formats

| Name (other names, sponsoring organizations) | BsAb format | Targets | Proposed mechanisms of action | Development stages | Diseases (or healthy volunteers) |
|---|---|---|---|---|---|
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-7A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds increase HSA to increase half-life | Phase I/II | Rheumatoid arthritis |

TABLE C-continued

Bispecific Formats

| Name (other names, sponsoring organizations) | BsAb format | Targets | Proposed mechanisms of action | Development stages | Diseases (or healthy volunteers) |
|---|---|---|---|---|---|
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. An impeller usable in a variable diameter bioreactor having multiple vessel sections of successively increasing or decreasing volume, the impeller comprising:
   an impeller blade having an edge extending along an impeller blade axis between first and second axial ends and having opposed impeller blade faces, an impeller blade leading edge, and an impeller blade trailing edge;
   wherein the leading and trailing edges each define a helix or spiral between the first and second axial ends of the impeller blade;
   wherein the impeller blade is one of at least two impeller blades that are each joined together along an axially extending impeller shaft; and
   wherein the at least two impeller blades are attached to the impeller shaft.

2. The impeller according to claim 1, wherein the helix or spiral has a pitch approximately equal to one half of a length between the first and second axial ends.

3. The impeller according to claim 1, wherein the helix or spiral has a pitch higher than one half of a length between the first and second axial ends.

4. The impeller according to claim 1, wherein the helix or spiral has a pitch lower than one half of a length between the first and second axial ends.

5. An impeller usable in a bioreactor, the impeller comprising:
   an impeller blade having an edge extending along an impeller blade axis between first and second axial ends and having opposed impeller blade faces, an impeller blade leading edge, and an impeller blade trialing edge, wherein
   the leading and trailing edges each define a helix or spiral between the first and second axial ends of the impeller blade,
      wherein the impeller blade is one of at least two impeller blades that are each joined together along an axially extending impeller shaft; and
   wherein the at least two impeller blades are attached to the impeller shaft.

6. The impeller according to claim 5, wherein the helix or spiral has a pitch approximately equal to one half of a length between the first and second axial ends.

7. The impeller according to claim 5, wherein the helix or spiral has a pitch higher than one half of a length between the first and second axial ends.

8. The impeller according to claim 5, wherein the helix or spiral has a pitch lower than one half of a length between the first and second axial ends.

9. A variable diameter bioreactor comprising:
   a variable diameter bioreactor having multiple vessel sections of successively increasing or decreasing volume; and
   an impeller having an impeller shaft and an impeller blade, the impeller blade having an edge extending along the impeller shaft between the first and second axial ends of the shaft and having opposed impeller blade faces, an impeller blade leading edge, and an impeller blade trailing edge, wherein
   the leading and trailing edges each define a helix or spiral between the first and second axial ends of the impeller blade,
   wherein the impeller blade is one of at least two impeller blades that are each joined together along an axially extending impeller shaft; and
   wherein the at least two impeller blades are attached to the impeller shaft.

10. The variable diameter bioreactor arrangement according to claim 9, wherein the helix or spiral has a pitch approximately equal to one half of a length between the first and second axial ends.

11. The variable diameter bioreactor arrangement according to claim 9, wherein the helix or spiral has a pitch higher than one half of a length between the first and second axial ends.

12. The variable diameter bioreactor arrangement according to claim 9, wherein the helix or spiral has a pitch lower than one half of a length between the first and second axial ends.

13. A process for treating a microorganism culture comprising:
   placing a fluid containing the microorganism culture in a variable diameter bioreactor arrangement, including a variable diameter bioreactor having multiple vessel sections of successively increasing or decreasing volume and an impeller having an impeller shaft, an impeller blade having an edge extending along the impeller shaft between first and second axial ends of the shaft and including opposed impeller blade faces, an impeller blade leading edge, and an impeller blade trailing edge, with the leading and trailing edges each defining a helix or spiral between the first and second axial ends of the impeller blade; and rotating the impeller in the fluid containing the microorganism culture;

wherein the impeller blade is one of at least two impeller blades that are each joined together along an axially extending impeller shaft; and wherein the at least two impeller blades are attached to the impeller shaft.

14. The process according to claim 13, wherein the impeller is rotated at a rate of 54-75 rpm.

15. The process according to claim 13, wherein the variable diameter reactor has a 20,000 liter fluid capacity.

* * * * *